(12) United States Patent
Kelly et al.

(10) Patent No.: US 9,993,648 B2
(45) Date of Patent: Jun. 12, 2018

(54) MEDICAL DEVICE DELIVERY SYSTEM

(71) Applicant: Medtronic, Inc., Minneapolis, MN (US)

(72) Inventors: Tomas K Kelly, Galway (IE); Paula McDonnell, Galway (IE); Sean Ward, Dublin (IE); Richard McEvoy, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 186 days.

(21) Appl. No.: 14/741,656

(22) Filed: Jun. 17, 2015

(65) Prior Publication Data

US 2016/0279423 A1   Sep. 29, 2016

Related U.S. Application Data

(60) Provisional application No. 62/139,357, filed on Mar. 27, 2015, provisional application No. 62/153,611, filed on Apr. 28, 2015.

(51) Int. Cl.
*A61B 19/00* (2006.01)
*A61N 1/372* (2006.01)
(Continued)

(52) U.S. Cl.
CPC ......... *A61N 1/372* (2013.01); *A61M 25/0105* (2013.01); *A61M 25/0136* (2013.01);
(Continued)

(58) Field of Classification Search
CPC .... A61N 1/372; A61N 1/0573; A61N 1/3756; A61N 1/375; A61N 1/059;
(Continued)

(56) References Cited

U.S. PATENT DOCUMENTS 8,236,016 B2 *  8/2012  To ................... A61B 17/320758
                                                606/159
8,744,572 B1    6/2014  Greenhut et al.
(Continued)

FOREIGN PATENT DOCUMENTS

WO    2012/082755 A1    6/2012

OTHER PUBLICATIONS (PCT/US2016/024160) PCT Notification of Transmittal of the International Search Report and the Written Opinion of the International Searching Authority, dated Jul. 6, 2016, 12 pages.

*Primary Examiner* — Son Dang

(57) ABSTRACT

The disclosure describes techniques and systems for delivering an implantable medical device. In one example, an implantable medical device (IMD) delivery system may include an elongated member comprising a first distal end configured to mate with the IMD, a resilient member disposed along at least a portion of the elongated member, a housing configured to accept a first proximal end of the elongated member and a second proximal end of the resilient member, a rotation control mechanism wherein user movement of the rotation control mechanism causes rotation of the elongated member with respect to the housing and a fixation element of the IMD into tissue, and a deflection control mechanism wherein user movement of the deflection control mechanism causes longitudinal displacement of the resilient member along a longitudinal axis of the elongated member and the housing resulting in angular deflection of the first distal end of the elongated member.

14 Claims, 24 Drawing Sheets

(51) Int. Cl.
*A61N 1/05* (2006.01)
*A61N 1/375* (2006.01)
*A61M 25/01* (2006.01)
*A61M 25/00* (2006.01)

(52) U.S. Cl.
CPC ........... *A61M 25/0147* (2013.01); *A61N 1/05* (2013.01); *A61N 1/059* (2013.01); *A61N 1/0573* (2013.01); *A61N 1/375* (2013.01); *A61N 1/3756* (2013.01); *A61N 1/37205* (2013.01); *A61M 25/0082* (2013.01); *A61N 2001/0578* (2013.01)

(58) Field of Classification Search
CPC ....... A61N 1/37205; A61N 2001/0578; A61M 25/0105; A61M 25/0147; A61M 25/0136; A61M 25/0082
See application file for complete search history.

(56) References Cited

U.S. PATENT DOCUMENTS

| | | | |
|---|---|---|---|
| 9,174,022 B2* | 11/2015 | Uihlein | A61B 1/0053 |
| 9,174,024 B1* | 11/2015 | Romoscanu | A61M 25/0136 |
| 2002/0065485 A1* | 5/2002 | DuBois | A61M 25/0136 |
| | | | 604/95.04 |
| 2005/0004644 A1* | 1/2005 | Kelsch | A61B 17/8888 |
| | | | 607/131 |
| 2005/0277874 A1* | 12/2005 | Selkee | A61M 25/0136 |
| | | | 604/95.04 |
| 2005/0277875 A1* | 12/2005 | Selkee | A61M 25/0136 |
| | | | 604/95.04 |
| 2007/0038052 A1* | 2/2007 | Swoyer | A61N 1/0551 |
| | | | 600/345 |
| 2009/0054963 A1* | 2/2009 | Osypka | A61N 1/057 |
| | | | 607/127 |
| 2010/0274338 A1* | 10/2010 | Ollivier | A61N 1/0573 |
| | | | 607/127 |
| 2011/0054287 A1* | 3/2011 | Schultz | A61B 5/0422 |
| | | | 600/374 |
| 2011/0054446 A1* | 3/2011 | Schultz | A61B 5/04 |
| | | | 604/528 |
| 2011/0251554 A1* | 10/2011 | Romoscanu | A61M 25/0136 |
| | | | 604/95.04 |
| 2012/0095539 A1 | 4/2012 | Khairkhahan et al. | |
| 2012/0172703 A1* | 7/2012 | Esguerra | A61B 5/062 |
| | | | 600/409 |
| 2012/0232563 A1* | 9/2012 | Williams | A61M 25/0108 |
| | | | 606/129 |
| 2013/0079798 A1* | 3/2013 | Tran | A61N 1/37205 |
| | | | 606/129 |
| 2013/0103047 A1* | 4/2013 | Steingisser | A61N 1/3756 |
| | | | 606/129 |
| 2013/0131591 A1* | 5/2013 | Berthiaume | A61N 1/3756 |
| | | | 604/95.04 |
| 2013/0131693 A1* | 5/2013 | Berthiaume | A61N 1/3756 |
| | | | 606/129 |
| 2013/0158379 A1* | 6/2013 | Selkee | A61B 1/0052 |
| | | | 600/373 |
| 2013/0172813 A1* | 7/2013 | Caples | A61B 18/1492 |
| | | | 604/95.04 |
| 2014/0031836 A1 | 1/2014 | Ollivier | |
| 2014/0135688 A1* | 5/2014 | Selkee | A61M 25/0144 |
| | | | 604/95.04 |
| 2015/0051682 A1 | 2/2015 | Schmidt et al. | |
| 2015/0105809 A1* | 4/2015 | Connolly | A61M 25/0136 |
| | | | 606/159 |
| 2016/0206853 A1* | 7/2016 | Bolduc | A61M 25/0147 |
| 2016/0331933 A1* | 11/2016 | Knutsen | A61M 25/0147 |
| 2018/0001058 A1* | 1/2018 | Schlesinger | A61M 25/0147 |

* cited by examiner

MEDICAL DEVICE DELIVERY SYSTEM

CROSS-REFERENCE TO RELATED APPLICATIONS

This application claims the benefit of U.S. Provisional Application No. 62/139,357 filed on Mar. 27, 2015 and 62/153,611, filed on Apr. 28, 2015. The disclosure of the above application is incorporated herein by reference in its entirety.

TECHNICAL FIELD

The disclosure relates to delivery systems and, more particularly, delivery systems that deliver medical devices.

BACKGROUND

Some medical devices may be implanted within a patient. These implantable medical devices (IMDs) may be implanted at target locations selected to detect a physiological condition of the patient and/or deliver one or more therapies. For example, electrical leads may be delivered to locations within an atria or ventricle to sense intrinsic cardiac signals and deliver pacing or antitachyarrhythmia shock therapy from a stimulation generator coupled to the electrical lead. In other examples, electrical leads may be tunneled to locations adjacent a spinal cord or other nerves for delivering pain therapy from a stimulation generator coupled to the lead. An electrical lead or drug delivery catheter may include a fixation element to secure the distal end of the lead or catheter at the target location.

SUMMARY

In general, the disclosure describes techniques, devices, and systems for delivering an implantable medical device (IMD) to a target location of a patient. For example, an IMD (e.g., a leadless pacing device) may need to be secured to an internal tissue or organ in order to monitor a patient condition and/or deliver therapy to the patient. A delivery system may include an elongated member (e.g., a sheath or catheter) configured to couple to the IMD and articulate to navigate within the patient to arrive at a target location. For an IMD that includes a helical fixation element requiring rotation to insert the helical fixation element into tissue, the delivery system may be configured to rotate the elongated member and cause rotation of the IMD and helical fixation element with respect to the tissue. A housing of the delivery system may include handle portion and couple to the elongated member via a rotation control mechanism such that user rotation of the rotation control mechanism can rotate the elongated member and the helical fixation element to secure the IMD to the tissue. The delivery system may also include a deflection control mechanism that causes angular deflection of a distal end of the elongated member to facilitate navigation within patient anatomy.

In one example, the disclosure is directed to an implantable medical device delivery system, the system including an elongated member comprising a first distal end and a first proximal end, the distal end configured to mate with an implantable medical device having a fixation element, a resilient member defining a second distal end and a second proximal end, the resilient member disposed along at least a portion of the elongated member, a housing configured to accept the first proximal end of the elongated member and the second proximal end of the resilient member, a rotation control mechanism coupled to the housing and a portion of the elongated member, wherein user movement of the rotation control mechanism causes rotation of the elongated member with respect to the housing for rotating the fixation element of the implantable medical device into tissue, and a deflection control mechanism coupled to the housing and the second proximal end of the resilient member, wherein user movement of the deflection control mechanism causes longitudinal displacement of the resilient member along a longitudinal axis of the elongated member and the housing resulting in angular deflection of the first distal end of the elongated member.

In another example, the disclosure is directed to a method for operating a delivery system for an implantable medical device, the method including manipulating a deflection control mechanism to cause longitudinal displacement of a resilient member along a longitudinal axis of an elongated member and a housing resulting in angular deflection of a distal end of the elongated member, the elongated member comprising the first distal end and a first proximal end, the distal end configured to mate with the implantable medical device having a fixation element, the resilient member defining a second distal end and a second proximal end, the resilient member disposed along at least a portion of the elongated member, the housing configured to accept the first proximal end of the elongated member and the second proximal end of the resilient member, the deflection control mechanism coupled to the housing and the second proximal end of the resilient member, and manipulating a rotation control mechanism coupled to the housing and a portion of the elongated member to cause rotation of the elongated member with respect to the housing and rotation of the fixation element of the implantable medical device into tissue.

In another example, the disclosure is directed to a an implantable medical device delivery system, the system including an elongated member comprising a first distal end and a first proximal end, the distal end configured to mate with an implantable medical device having a fixation element, a resilient member defining a second distal end and a second proximal end, the resilient member disposed along at least a portion of the elongated member, means for housing the first proximal end of the elongated member and the second proximal end of the resilient member, means for rotating the elongated member with respect to the means for housing the first proximal end of the elongated member for rotating the fixation element of the implantable medical device into tissue, and means for deflecting the first distal end of the elongated member via longitudinal displacement of the resilient member along a longitudinal axis of the elongated member, the deflection being angular deflection of the first distal end of the elongated member.

The details of one or more examples are set forth in the accompanying drawings and the description below. Other features, objects, and advantages of the disclosure will be apparent from the description and drawings, and from the claims.

DETAILED DESCRIPTION

Figure 1:
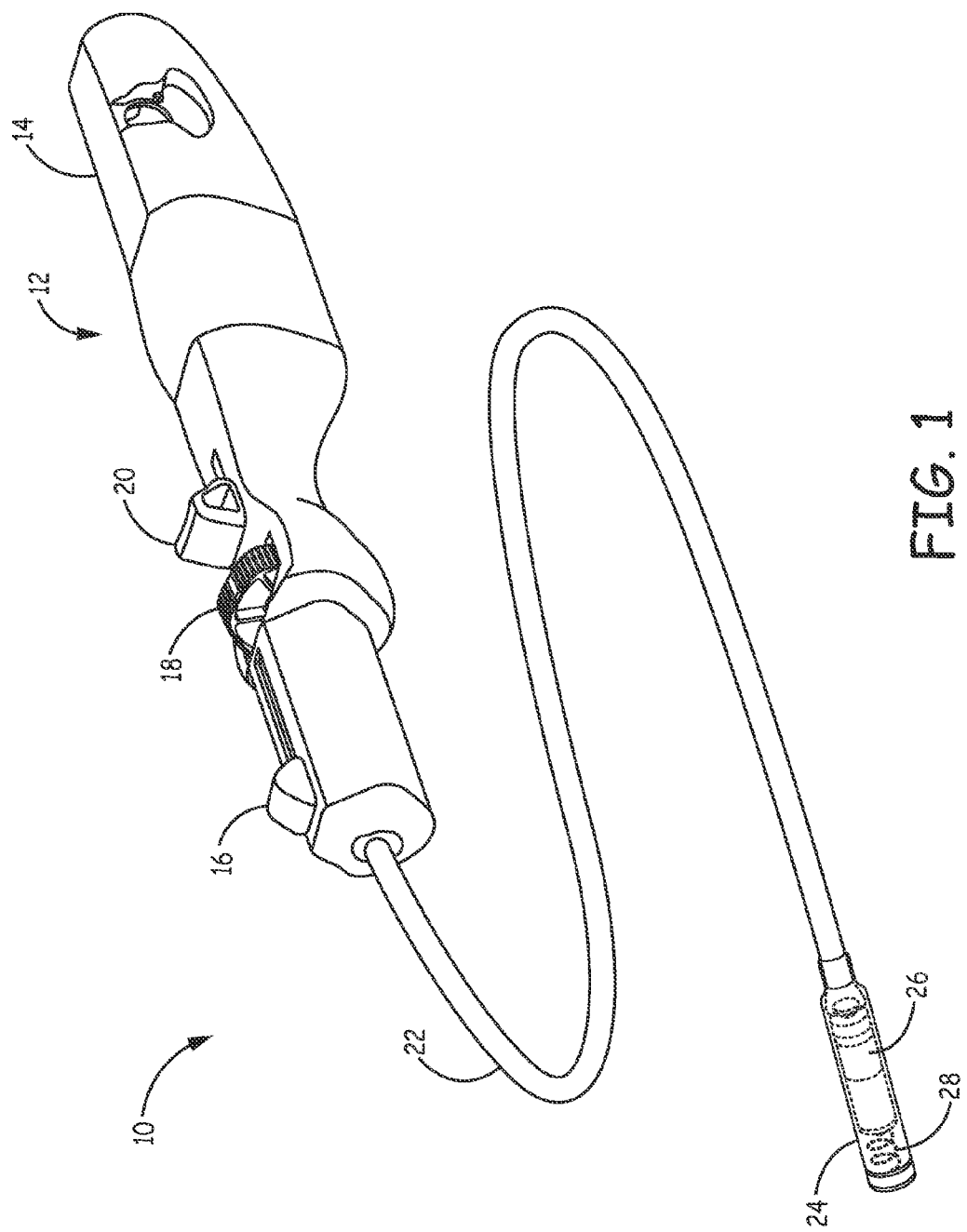
FIG. 1 is a conceptual drawing illustrating an example delivery system for delivering an implantable medical device (IMD) comprising a helical fixation element.

FIG. 1 is a conceptual drawing illustrating an example delivery system 10 for delivering an implantable medical device (IMD) 26 comprising a helical fixation element 28. This disclosure describes techniques and systems, such as delivery system 10, for delivering IMDs (e.g., IMD 26) to target tissue locations within a patient. Some IMDs are relatively small devices that are intended to be implanted at target tissue locations deep within the anatomy of a patient. Generally, IMDs may be implanted within the heart, vasculature, or other organs and secured to the target tissue location with one or more fixation elements such as barbs, hooks, and/or adhesives.

An IMD may be configured as a leadless pacing device configured to be implanted within a chamber of the heart. The leadless pacing device may be configured to monitor physiological signals and/or deliver pacing pulses, as some examples. Generally, a leadless pacing device may include one or more fixation elements in the shape of a J-shaped hook that pierces into the target tissue location (e.g., a ventricle wall) and secures the leadless pacing device to the tissue. A delivery system may deliver the leadless pacing device to the target tissue location with the hooks in a substantially straight configuration with the distal ends of the hooks biased against an outer sheath. When the leadless pacing device is positioned adjacent to the target tissue location, a user may withdraw the outer sheath of the delivery system to expose the hooks such that the hooks pierce the target tissue and return to the J-shape to secure the leadless pacing device to the tissue. However, at some anatomical locations, the target tissue may be thin, delicate, previously damaged, or otherwise at risk for tearing from the use of the hooks described above. Therefore, a leadless pacing device with a hook-type fixation element may not be suitable for certain target tissue locations.

As described herein, a delivery system 10 is configured to deliver IMD 26 having a helical fixation element 28 or other fixation element that secures to tissue using circumferential rotation with respect to the tissue. Helical fixation elements may be more appropriate for thin or delicate tissues than hooks or other fixation elements that snap into a secured configuration. For example, rotation of the helical fixation element may cause minimal shear forces on the tissue thus reducing the risk of tissue tearing during insertion of the fixation element into the tissue. Delivery system 10 may be configured to rotate IMD 26 within the patient such that helical fixation element 28 can be inserted in the target tissue location. Delivery system 10 may provide this rotational functionality while also providing angular deflection of the distal end of the elongated member to facilitate navigation through tortuous portions of the anatomy between an insertion location in the skin of the patient to the target tissue location within the patient.

As shown in FIG. 1, delivery system 10 includes a housing 12 coupled to outer elongated member 22. Outer elongated member 22 comprises a distal end 24 configured to retain IMD 26. In the fully extended configuration, outer elongated member 22 covers the housing of IMD 26 and helical fixation element 28. Housing 12 may also be coupled to an inner elongated member (not shown) and a resilient member (not shown) within outer elongated member 22. The inner elongated member may be concentric with outer elongated member 22. Housing 12 may include slider 16 of a deployment mechanism, wheel 18 of a rotation control mechanism, slider 20 of a deflection control mechanism, and handle portion 14. Outer elongated member 22 is configured to be inserted within the patient and housing 12 is intended to remain outside of the patient to facilitate user manipulation of various controls of housing 12.

Figure 3:
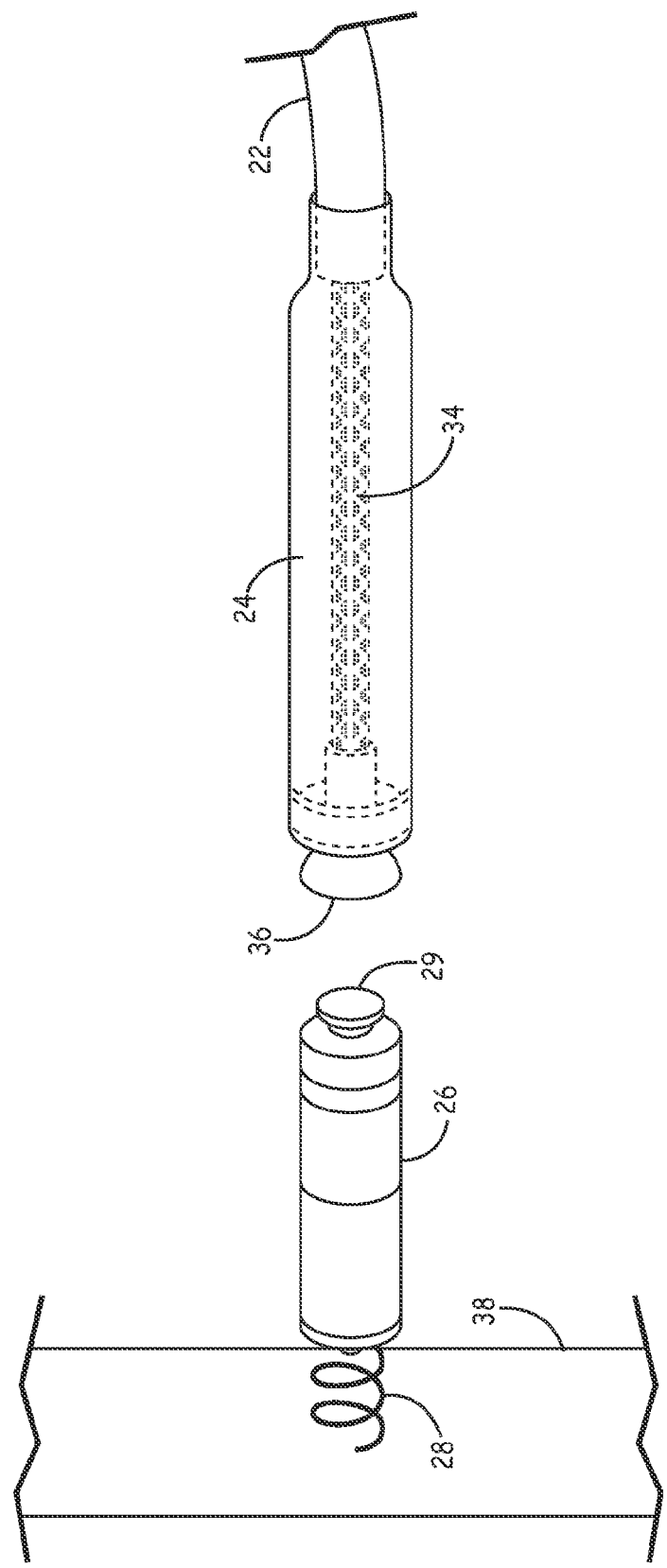
FIG. 3 is a conceptual drawing illustrating a distal end of the delivery system after the IMD has been delivered to a target tissue location.

The inner elongated member may include a first distal end and a first proximal end, where the first distal end is configured to mate with IMD 26 as shown in FIG. 3. The resilient member (e.g., a pull-wire) may define a second distal end and a second proximal end, where the resilient member is disposed along at least a portion of the inner elongated member. In some examples, the resilient member is disposed within a lumen defined by the inner elongated member or outside of the inner elongated member. The resilient member may be attached to a distal end of the inner elongated member at a location radially outward from a central longitudinal axis of the inner elongated member. In this manner, longitudinal displacement of the resilient member may cause angular deflection of the distal end of the inner elongated member and outer elongated member 22. In some examples, the resilient member may be attached directly to outer elongated member 22 instead of the inner elongated member. The resilient member may be constructed of a metal wire, a wire braid, a polymer, a composite material, or any other material being longitudinally inelastic and bendable in an angular direction. In some examples, two or more resilient members may be implemented at different circumferential positions to facilitate angular deflections in two or more different circumferential positions around the inner elongated member.

Housing 12 may be configured to accept the first proximal end of the inner elongated member and the second proximal end of the resilient member. In addition, housing 12 may be configured to accept the proximal end of outer elongated member 22. Housing 12 may be configured with various internal support structures for respective components. For example, housing 12 may support each of slider 16 of the deployment mechanism, wheel 18 of the rotation control mechanism, slider 20 of the deflection control mechanism, in addition to other components not shown within housing 12. Handle portion 14 may be configured to be held by a human hand such that a thumb of the user is positioned adjacent to one or more of slider 16, wheel 18, and slider 20.

The rotation control mechanism (e.g., wheel 18) is coupled to housing 12 and a portion of the inner elongated member. In this manner, user movement, or manipulation, of wheel 18 of the rotation control mechanism causes rotation of the inner elongated member with respect to housing 12. This rotation translates to rotation of IMD 26 and helical fixation element 28 within the distal end 24 of outer elongated member 22. As described herein, the rotation control mechanism may include different structures for causing the inner elongated member to rotate. The rotation control mechanism, various examples of which are described herein, may include any means for rotating the inner elongated member with respect to housing 12.

The deflection control mechanism (e.g., slider 20) is also coupled to housing 12 and the second proximal end of the resilient member, as shown herein. In this manner, user movement, or manipulation, of slider 20 causes longitudinal displacement of the resilient member (e.g., a pull-wire) along a longitudinal axis of the inner elongated member, outer elongated member 22, and housing 12 resulting in angular deflection of the first distal end of the inner elongated member and distal end 24 of outer elongated member 22.

In addition, the deflection control mechanism may be configured to allow rotation of the resilient member about the longitudinal axis to match rotation of the inner elongated member caused by user movement of the rotation control mechanism (e.g., wheel 18). In other words, rotation of the inner elongated member will include rotation of the resilient member such that the resilient member does not get twisted around or within the inner elongated member during rotation. As described herein, the deflection control mechanism may include different types of sliders and other structures for causing longitudinal displacement of the resilient member. The deflection control mechanism, various examples of which are described herein, may include any means for deflecting the distal end of the inner elongated member via longitudinal displacement of the resilient member along a longitudinal axis of the inner elongated member.

Although an inner elongated member and an outer elongated member are described herein, outer elongated member 22 may not be necessary in some examples. Instead, the inner elongated member being configured to mate with IMD 26 and rotate with respect to housing 12 may be sufficient to adequately deliver IMD 26 to the target tissue location. The deployment mechanism, that includes slider 16, may be removed from housing 12 if outer elongated member 22 is not included in system 10. Alternatively, the deployment mechanism may be coupled to another longitudinally movable element that assists in the deployment of IMD 26 from delivery system 10.

As described herein, manipulation of the rotation control mechanism (e.g., wheel 18) to rotate the inner elongated member causes helical fixation element 28 of IMD 26 to be inserted into tissue of a patient. However, the fixation element attached to IMD 26 may not need to be helical while still benefitting from IMD rotation to secure the fixation element to the tissue. For example, a fixation element may include one or more barbs, protrusions, or features extending distally, circumferentially, and/or radially from the housing of IMD 26. Each of these elements may be configured to fix to or embed within tissue in response to rotation of the inner elongated member and that rotation being translated to the housing of IMD 26.

In one example, IMD 26 may include a pair of electrodes carried on the housing of IMD 26. An example cardiac pacing device is described in U.S. Pat. No. 8,744,572 to Greenhut et al., entitled "SYSTEMS AND METHODS FOR LEADLESS PACING AND SHOCK THERAPY," the entire content of which is incorporated herein by reference. Since IMD 26 may include two or more electrodes carried on the exterior of its housing, no other leads or structures may need to reside in other chambers of the heart. In other words, such an IMD may be referred to as a leadless pacing device. In other examples, IMD 26 may be any other type of medical device that may include electrode, sensors, drug delivery ports, or any other such monitoring and/or therapy delivery mechanism.

IMD 26 may be implanted in any structure of the heart or other organ. As some examples, IMD 26 with use helical fixation element 28 to be implanted in the right atrial appendage, atrial septum, floor of the right atrium, or christa terminalis. Helical fixation element 28 may be configured to secure IMD 26 to tissue and retain an electrode (e.g., a cathode or anode) in contact with cardiac tissue. In other examples, helical fixation element 28 may itself function as an electrode. However, IMD 26 may be fixed to other tissues of the right atrium, left atrium, right ventricle, or left ventricle in other examples. In addition, IMD 26 may use helical fixation element 28 to be implanted within a vessel or on an exterior surface of the heart. IMD 26 is not limited to cardiac functions, however, and delivery system 10 may be configured to deliver IMD 26 to any anatomical location within the patient.

Although the delivery systems are described herein for delivery an IMD having a helical fixation element, the delivery systems may also be configured to deliver IMDs with different types of fixation elements. For example, the delivery systems may be configured to deliver IMDs having one or more hooks that curl outward upon withdrawal on the outer elongated member from the hooks. In this manner, the delivery systems may not require use of the rotation control mechanisms for delivering IMDs without a helical fixation element. However, the rotation control mechanism may still be used by a user to circumferentially orient the IMD to the target tissue location prior to deploying the fixation elements.

Figure 2:
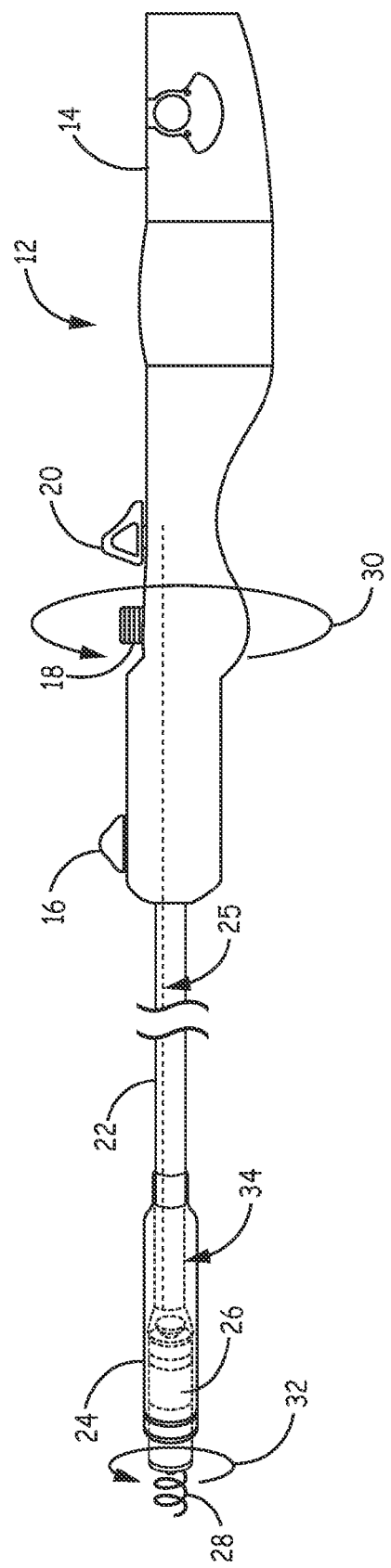
FIG. 2 is a conceptual drawing illustrating the example delivery system of FIG. 1 having a rotation control mechanism for rotating the IMD.

FIG. 2 is a conceptual drawing illustrating the example delivery system 12 of FIG. 1 having a rotation control mechanism for rotating IMD 26. As shown in FIG. 2, rotation of rotation control mechanism (e.g., wheel 18) in the direction of arrow 30 will translate into rotation of inner elongated member 34, IMD 26, and helical fixation element 28 in the direction of arrow 32. In this manner, torque applied to wheel 18 by a finger or thumb of a user is translated by the rotation control mechanism and inner elongated member 34 to insertion torque for helical fixation element 28. The rotation control mechanism may translate torque to IMD 26 whether inner elongated member 34 and outer elongated member 22 are substantially straight or curved at one or more locations as would be typical once the elongated members are disposed within patient anatomy.

The direction of rotation of wheel 18 and inner elongated member 34 may be the same. However, in some examples, the rotation control mechanism may use one or more gears to rotate inner elongated member 34 in a direction opposite to wheel 18. Opposing directions of rotation may be used for ergonomic reasons (e.g., right-handedness or left-handedness) of the user of housing 12 and/or to accommodate the helical orientation of helical fixation element 28.

The deployment mechanism (e.g., slider 16) may control how much of IMD 26 and helical fixation element 28 is exposed out from the distal end 24 of outer elongated member 22. In the fully extended position, outer elongated member 22 may fully cover helical fixation element 28 to protect IMD 26 and the patient from inadvertent strikes of helical fixation element 28 against tissue as IMD 26 is navigated through patient anatomy towards the target tissue location. The deployment mechanism may be coupled to housing 12 and a proximal end of outer elongated member 22 within housing 12. The deployment mechanism may include slider 16 coupled to the proximal end of outer elongated member 22 and defining an aperture through which the inner elongated member 34 is allowed to rotate, wherein user movement of the deployment mechanism causes longitudinal displacement of slider 16 and outer elongated member 22 along the longitudinal axis with respect to housing 12 and inner elongated member 34.

In this manner, proximal movement of outer elongated member 22 by manipulation of slider 16 exposes at least a portion of helical fixation element 28 of IMD 26. As shown in FIG. 2, the deployment mechanism has been manipulated to withdraw distal end 24 of outer elongated member 22. Now that helical fixation element 28 is exposed, rotation of helical fixation element 28 against target tissue will cause the helical fixation element to insert itself within the tissue. Full manipulation of the deployment mechanism may cause additional, or even complete, withdrawal of outer elongated member 22 from the housing of IMD 26. In other examples, once helical fixation element 28 has been rotated and fully fixed to tissue, the remainder of the housing of IMD 26 within the distal end 24 may be pulled out of distal end 24. In some examples, a tether may need to be released between IMD 26 and housing 12 that otherwise retains IMD 26 against the distal end of inner elongated member 34.

FIG. 3 is a conceptual drawing illustrating a distal end of the delivery system after IMD 26 has been rotated and delivered to target tissue location 38. As shown in FIG. 3, helical fixation element 28 is fully inserted into target tissue location 38. After IMD 26 is fixed to tissue, the user may manipulate the deployment mechanism to fully withdraw distal end 24 of outer elongated member 22 along inner elongated member 34. As shown in FIG. 3, distal end 36 of inner elongated member 34 thus extends distally of the distal end 24 of outer elongated member 22. However, in other examples, inner elongated member 34 may not extend distal of distal end 24 to deliver IMD 26. Prior to disengagement from distal end 36, keyed structure 29 of IMD 26 may mate to a keyed surface of distal end of 36 of inner elongated member 34. The mating of keyed structure 29 to the keyed surface may allow rotational torque to transfer from inner elongated member 34 to IMD 26 and helical fixation element 28.

IMD 26 may include a housing, or case, a proximal cap that may include keyed structure 29, helical fixation element 28, and two or more electrodes, in one example. The case and cap may enclose and protect the various electrical components within IMD 26. The two or more electrodes may be carried on the housing created by the case and cap. In this manner, the electrodes may be considered leadless electrodes. In one example, one electrode may be disposed on the exterior of the housing that does not contact tissue location 38. Another electrode may be a circular electrode positioned on the distal end of the housing of IMD 26 and configured to contact tissue when helical fixation element 28 is fully inserted. In some examples, helical fixation element may be configured as one of the electrodes. Three or more electrodes may be carried by IMD 26 in some examples. The electrodes may be used as cathodes or anodes, and used to monitor intrinsic electrical signals and/or deliver electrical signals for therapy and/or diagnostic purposes.

Figure 4:
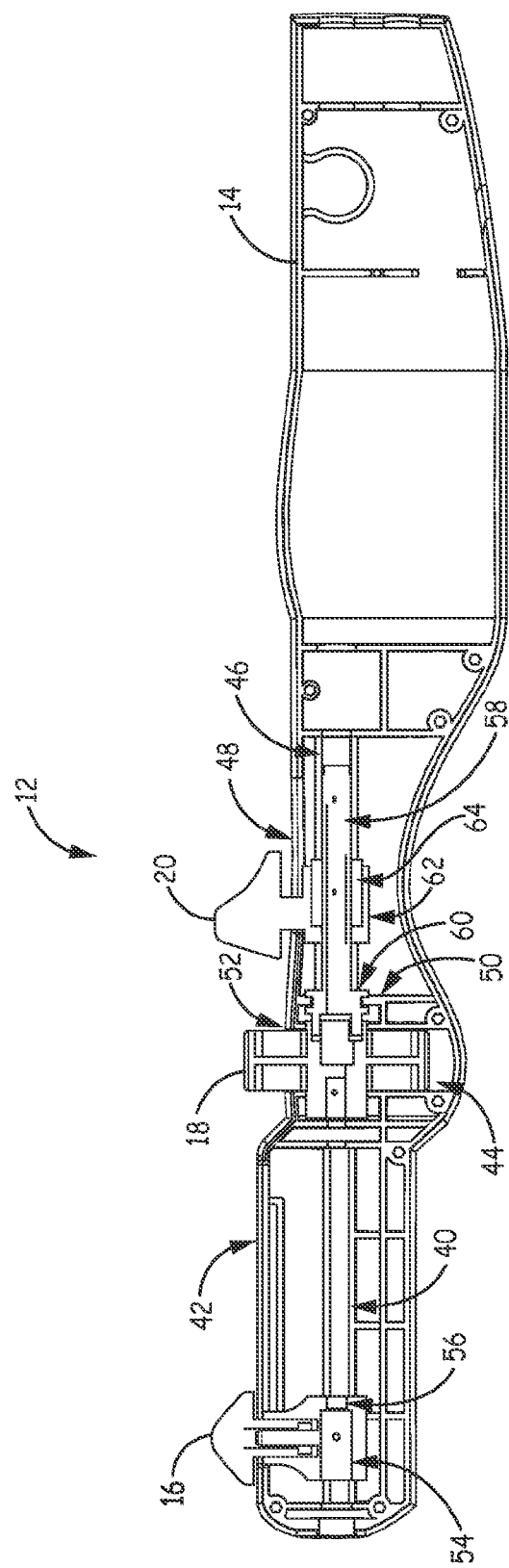
FIG. 4 is a cross-sectional view of an example housing of a delivery system.

FIG. 4 is a cross-sectional view of the interior of example housing 12 of delivery system 10 shown in FIGS. 1 and 2. The components associated with housing 12 as described in FIGS. 4, 5A, 5B, 6A, and 6B are examples of components that may achieve the functionality described herein. Therefore, some components may be altered to achieve different shapes or dimensions while still maintaining the functionality described herein with respect to the deployment mechanism, the rotation control mechanism, and the deflection control mechanism.

As shown in FIG. 4, housing 12 supports a deployment mechanism, a rotation control mechanism, and a deflection control mechanism. The deployment mechanism includes slider 16 that includes an external button for manipulation by a user and defines channel 54 and channel 56. Slider 16 is configured to accept and fix the proximal end of outer elongated member 22 within channel 54. Slider 16 is also configured to accept inner elongated member 34 through channel 56 such that inner elongated member 34 is free to rotate within slider 16 and outer elongated member 22.

Housing 12 defines track 40 that mates to an outer surface of slider 16 to constrain movement of slider 16 to a linear path. Housing 12 also defines slot 42 through which a portion of slider 16 extends out from housing 12. Manipulation of slider 16 towards handle 14 along the longitudinal axis of housing 12 causes outer elongated member 22 to move in the same direction with respect to housing 12 and inner elongated member 34.

The deflection control mechanism includes slider 20, shaft 58, and collar 64. Slider 20 is configured to move along the longitudinal axis of housing 12. Slider 20 comprises a protrusion extending out from the housing for manipulation by a user and a cylinder 62 attached to the protrusion. Housing 12 defines track 46 that engages with an outer surface of slider 20 retain slider 20 along a liner path within housing 12. Housing 12 also includes slot 48 through which the protrusion of slider 20 extends out of housing 12.

Shaft 58 comprises at least one rib 94 (shown in FIG. 5B) extending longitudinally along an exterior surface of shaft 58, wherein at least a portion of shaft 58 is disposed within cylinder 62 of slider 20. Shaft 58 may also include flanges 60 that mate to a retainer 50 defined by housing 12 and configured to allow shaft 58 to rotate about the longitudinal axis and prevent shaft 58 from moving axially along the longitudinal axis.

Collar 64 defines an aperture, at least one channel extending radially outward from the aperture and longitudinally along collar 64, and a mounting hole configured to mount the proximal end of the resilient member (e.g., a pull-wire). The at least one channel is configured to mate with the at least one rib 94 of shaft 58. In addition, at least a portion of collar 64 is disposed between cylinder 62 and shaft 58 such that collar 64 can rotate within cylinder 62 and slide longitudinally along shaft 58. Therefore, user movement of slider 20 in the longitudinal direction causes longitudinal displacement of collar 64 and the resilient member.

The rotation control mechanism may include wheel 18 coupled to housing 12 and at least partially exposed externally from housing 12 through opening 52 defined by housing 12. At least a portion of wheel 18 may reside within space 44 defined by housing 12. Wheel 18 is attached to and concentric with the inner elongated member 34, and wheel 18 is coupled to a distal end of shaft 58 of the deflection control mechanism such that rotation of wheel 18 causes rotation of shaft 58, collar 64, and the resilient member.

Figure 5A:
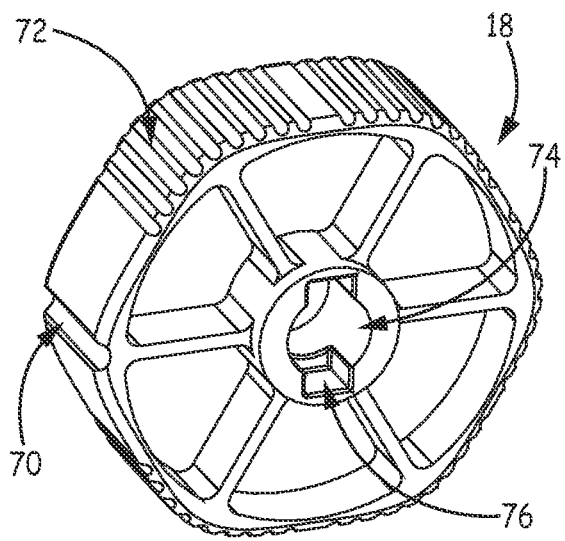
FIG. 5A is a conceptual drawing illustrating a wheel of a rotation control mechanism of the delivery system of FIG. 4.

FIG. 5A is a conceptual drawing illustrating wheel 18 of the rotation control mechanism of the delivery system 10 of FIG. 4. As shown in FIG. 5A, wheel 18 may define a central channel 74 configured to attach to a portion of inner elongated member 34. For example, an adhesive and/or a mechanism fixation mechanism may be used to attach the inner elongated member to wheel 18. Wheel 18 also defines female locking structure 76 configured to mate with male locking structure 92 (FIG. 5B) of the distal end of shaft 58. Female locking structure 76 and male locking structure 92 ensure wheel 18 and shaft 58 both rotate at the same angular velocity.

Wheel 18 also defines outer ridges 72 configured to increase the coefficient of friction between wheel 18 and a finger of the user. In addition, wheel 18 defines a marker channel at one circumferential location on the outer surface of the wheel. The user may use the marker channel as a visual indication of angular rotation of wheel 18. For example, when referenced to an outer surface of housing 12, the distance between the marker channel reappearing when wheel 18 is rotated is one complete revolution or 360 degrees of angular rotation.

Figure 5B:
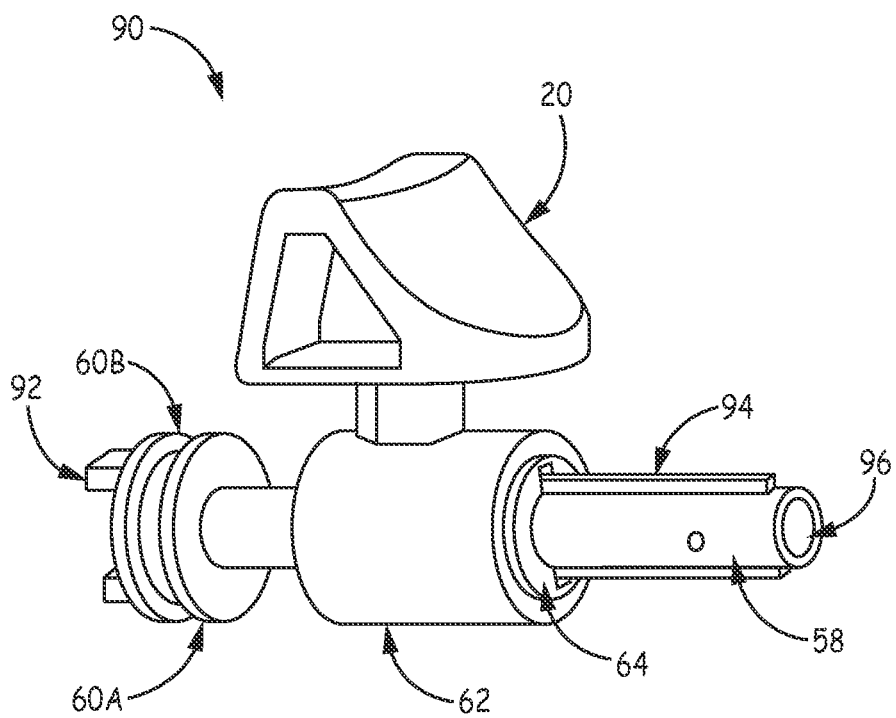
FIG. 5B is a perspective view of a slider, a shaft, and a collar of a deflection control mechanism of the delivery system of FIG. 4.

FIG. 5B is a perspective view of slider 20, shaft 58, and collar 64 of a deflection control mechanism 90 of the delivery system 10 of FIG. 4. As shown in FIG. 5B, slider 20 comprises cylinder 62, through which both collar 64 and shaft 58 reside. Shaft 58 defines ribs 94 that engage with respective channels 104 (shown in FIG. 6B) of collar 64 to ensure that collar 64 rotates with shaft 58. However, ribs 94 also allow collar 64 to move longitudinally, or axially, along shaft 58. Shaft 58 also defines flanges 60A and 60B configured to reside on opposite sides of retaining 50 of housing 12. Male structures 92 mate to female structures 76 of wheel 18.

Since the resilient member (e.g., pull-wire) is coupled to collar 64, these features allow the resilient member to rotate with inner elongated member 34 while translating longitudinally to cause the distal end of the inner elongated member to angularly deflect. Collar 64 may also define one or more radially extending flanges configured to mate with a respective channel defined by cylinder 62 to lock collar 64 axially with cylinder 62 while permitting collar 62 to rotate within cylinder 62. Alternatively, cylinder 62 may define one or more radially inward flanges that mate with respective channels in collar 64.

Figure 6A:
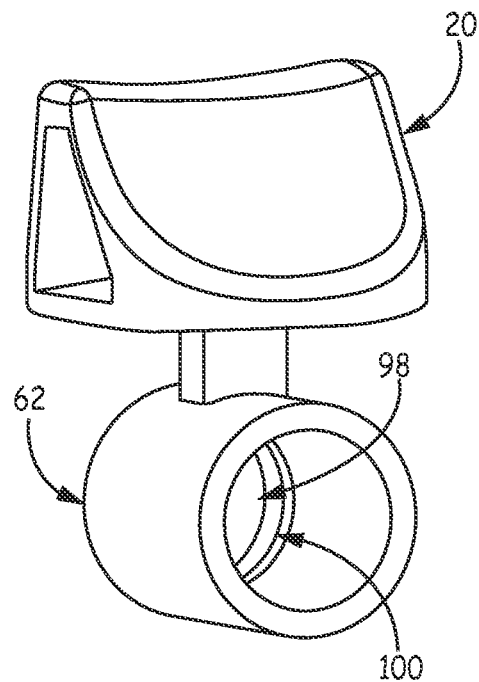
FIGS. 6A and 6B are perspective views of the slider and the collar, respectively, of the delivery system of FIG. 4.
Figure 6B:
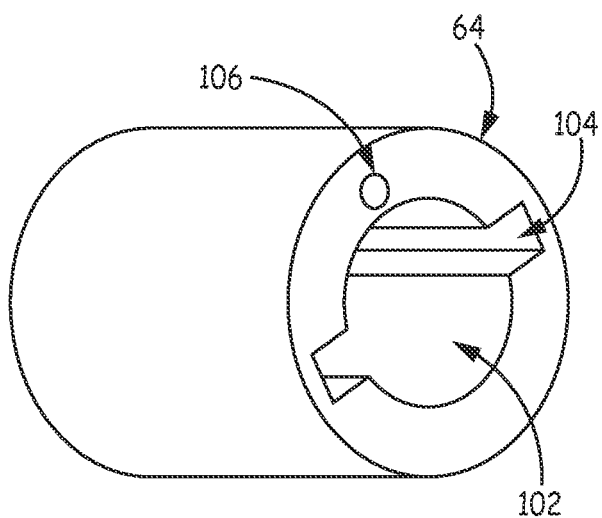

FIGS. 6A and 6B are perspective views of slider 20 and collar 62, respectively, of the delivery system 10 of FIG. 4. As shown in FIG. 6A, slider 20 includes cylinder 62. Cylinder defines a central opening 98 through which collar 62 and shaft 58 are disposed. In addition, cylinder 62 may define a flange 100 configured to retain collar 62 within cylinder 62.

As shown in FIG. 6B, collar 64 defines a lumen 102 through which shaft 58 is disposed. Collar 64 also defines channels 104 configured to mate with respective ribs 94 of shaft 58. Collar 64 also defines aperture 106 through which the resilient member is disposed. The resilient member may have a hydrotube crimped on the end of it to secure the resilient member within aperture 106. However, any other attachment mechanism such as adhesives, set pins, welding, overmolding, may be used to secure the resilient member. Aperture 106 is typically located radially outward from the center of collar 64 and at a single circumferential location of collar 64. In other examples, two or more apertures 106 may be used to secure respective resilient members.

Figure 7:
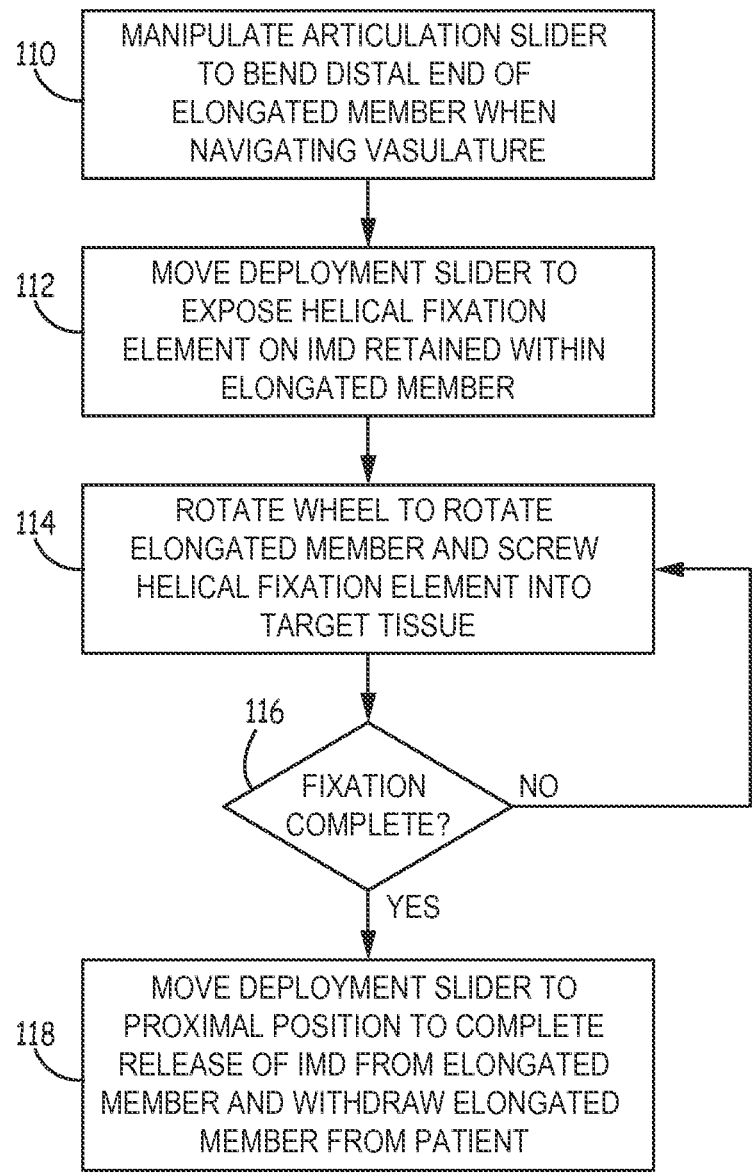
FIG. 7 is a flow diagram illustrating an example process for operating the delivery system of FIG. 4.

FIG. 7 is a flow diagram illustrating an example process for operating the delivery system 10 of FIG. 4. As shown in FIG. 7, a user may manipulate articulation slider 20 to bend the distal end of the inner elongated member 34, and outer elongated member 22, when navigating through patient vasculature or other anatomical structures (110). Once IMD 26 is located adjacent to target tissue location 38, the user may move the deployment slider 16 distally to expose helical fixation element 28 on IMD 28 still retained within outer elongated member 22 (112).

Next, the user makes contact between the helical fixation element 28 and the target tissue location 28 and rotates wheel 18 of the rotation control mechanism to screw helical fixation element 28 into the target tissue (114). The user may use a marker channel 70, audible clicks, or an automated rotation stop to determine progress of insertion of helical fixation element 28. If fixation is not yet complete ("NO" branch of block 116), the user may continue to rotate wheel 18 (114). If fixation of helical fixation element 28 is complete ("YES" branch of block 116), the user may move deployment slider 16 to the proximal position to complete the withdraw of outer elongated member 22 from IMD 26 to release IMD 26 from outer elongated member 22 and withdraw outer elongated member 22 and delivery system 10 from the patient (118).

In some examples, delivery system 10 may be used to retrieve IMD 26 after the IMD has been implanted. In this manner, the process for retrieval of IMD 26 of FIG. 7 may be reversed. In addition, or in other examples, a tether may be used to attach to IMD 26 and remove IMD 26 from the target tissue location 38.

Figure 8A:
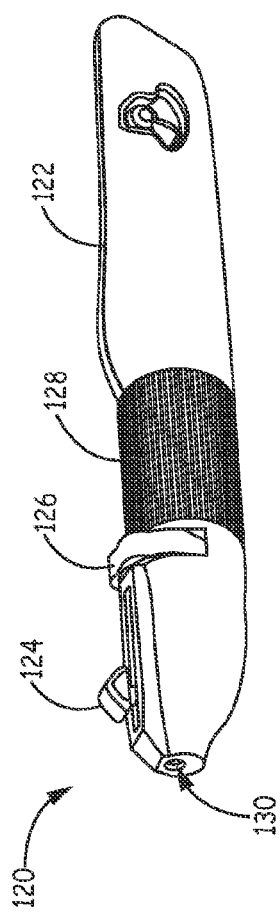
FIG. 8A is a perspective view of an example housing of a delivery system.

FIG. 8A is a perspective view of an example housing 120 of a delivery system similar to delivery system 10. Housing 120 may be similar to housing 12 described above. However, housing 120 may include a rotation control mechanism and a deflection control mechanism that vary from that of housing 12. Housing 120 may define an opening 130 through which inner elongated member 34 and, in some example, outer elongated member 22 may enter housing 120. Housing 120 may also be coupled to slider 124 of the deployment mechanism, wheel 126 of the rotation control mechanism, and exterior cylinder 128 of the deflection control mechanism. The entire external cylinder 128 may rotate about housing 120. However, only a partial circumference of external cylinder 128 may be exposed external from housing 120 in other examples. Housing 120 may also define handle 122.

Figure 8B:
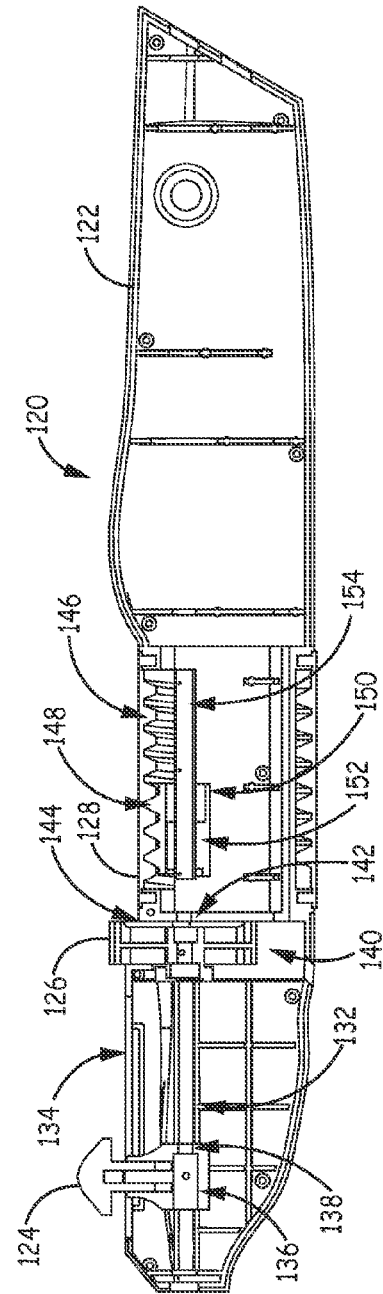
FIG. 8B is a cross-sectional view of the housing of the delivery system of FIG. 8A.

The components associated with housing 120 as described in FIGS. 8A, 8B, 9A, and 9B are examples of components that may achieve the functionality described herein. Therefore, some components may be altered to achieve different shapes or dimensions while still maintaining the functionality described herein with respect to the deployment mechanism, the rotation control mechanism, and the deflection control mechanism FIG. 8B is a cross-sectional view of the housing of the delivery system of FIG. 8A. As discussed above, housing 120 may be similar to housing 12 described above and include some similar components. For example, slider 124 may be substantially similar to slider 16 of FIGS. 1 and 4. In this manner, the deployment mechanism includes slider 124 that includes an external button for manipulation by a user and defines channel 136 and channel 138. Slider 124 is configured to accept and fix the proximal end of outer elongated member 22 within channel 136. Slider 124 is also configured to accept inner elongated member 34 through channel 138 such that inner elongated member 34 is free to rotate within slider 124 and outer elongated member 22.

Housing 120 defines track 132 that mates to an outer surface of slider 124 to retain slider 124 movement in a linear path. Housing 120 also defines slot 134 through which a portion of slider 124 extends out from housing 12. Manipulation of slider 124 towards handle 122 along the longitudinal axis of housing 120 causes outer elongated member 22 to move in the same direction with respect to housing 120 and inner elongated member 34.

Similar to the rotation control mechanism of housing 12, the rotation control mechanism of housing 120 may include a wheel 126 coupled to housing 120 and at least partially exposed externally from housing 120 through opening 144 defined by housing 120. At least a portion of wheel 126 may reside within space 140 defined by housing 120. Wheel 126 is attached to and concentric with the inner elongated member 34, and wheel 126 is coupled to a distal end of shaft 154 of the deflection control mechanism such that rotation of wheel 126 causes rotation of shaft 154, collar 152, and the resilient member. In this manner, wheel 126 may be similar to wheel 18.

The deflection control mechanism of housing 120 varies from the mechanism of housing 12. The deflection control mechanism of housing 120 includes external cylinder 128 that rotates instead of slider 20 of housing 12. In FIG. 9B, the deflection control mechanism includes external cylinder 128, slider 150, shaft 154, and collar 152. External cylinder 128 is at least partially external of housing 120, and external cylinder 128 includes a threaded structure 146 on an internal surface of the external cylinder.

Slider 150 is configured to move along the longitudinal axis of housing 120. Housing 120 also defines a track (not shown) that engages with an outer surface of slider 150 to retain slider 150 along a liner path within housing 120. Slider 150 also defines a cylinder having an aperture 158, and at least one ridge 156, or rib, running longitudinally along an external surface of the cylinder of slider 150. Ridge 156 may be configured to mate with a track defined by housing 120. Slider may also include a threaded structure 148 configured to mate with threaded structure 146 of external cylinder 128. In this manner rotation of external cylinder 128 causes linear movement of slider along the longitudinal axis and shaft 154.

Shaft 154 comprises at least one rib 160 (shown in FIG. 9B) extending longitudinally along an exterior surface of shaft 154, wherein at least a portion of shaft 154 is disposed within the cylinder defined by slider 150. Shaft 154 may also include a flanges or other structure that mate to a retainer 142 defined by housing 120 and configured to allow shaft 154 to rotate about the longitudinal axis and prevent shaft 154 from moving axially along the longitudinal axis.

Collar 152 defines an aperture, at least one channel extending radially outward from the aperture and longitudinally along collar 152, and a mounting hole configured to mount the proximal end of the resilient member (e.g., a pull-wire). The at least one channel is configured to mate with the at least one rib 160 of shaft 154. In addition, at least a portion of collar 152 is disposed between the cylinder of slider 150 and shaft 154 such that collar 152 can rotate within the cylinder of slider 150 and slide longitudinally along shaft 154. Therefore, user rotation of external cylinder 128 with respect to housing 120 causes longitudinal displacement of collar 152 and the resilient member. Although not explicitly shown, housing 120 defines structures required to mount each component of the rotation control mechanism and deflection control mechanism within housing 120.

Figure 9A:
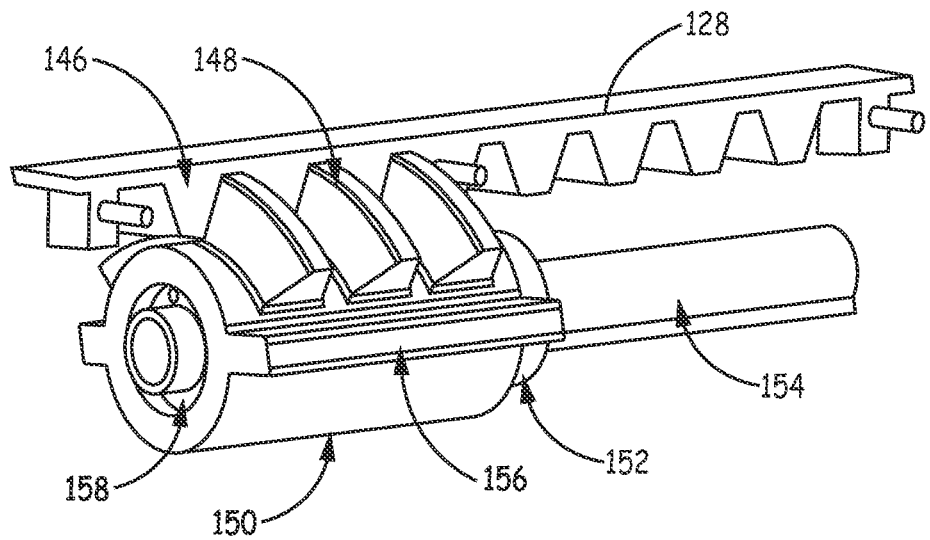
FIGS. 9A and 9B are perspective views of an external cylinder, a slider, a shaft, and a collar of an example deflection control mechanism of the delivery system of FIG. 8A.
Figure 9B:
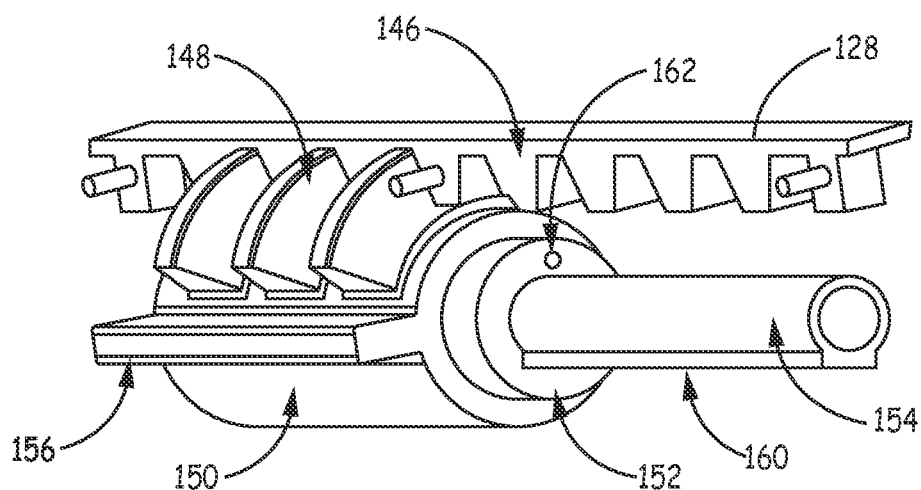

FIGS. 9A and 9B are perspective views of external cylinder 128, slider 150, shaft 152, and collar 152 of an example deflection control mechanism of the delivery system and housing 120 of FIG. 8A. As shown in FIG. 9A, external cylinder 128 is only shown as a cut-away portion to view the other components. External cylinder 128 includes threated structure 146 on an inner surface, the threaded structure 146 configured to mate with threaded structure 148 of slider 150. Slider 150 defines an opening 158 through which collar 152 is disposed. In addition, collar 152 defines an aperture through which shaft 154 is disposed.

Ridges 156 of slider 150 make to respective tracks (not shown) defined by housing 120 and shaft 154 is coupled to a portion of housing 120. In this manner, user rotation of external cylinder 128 causes threaded structures 146 to contact threaded structures 148 and translate the rotational movement of external cylinder 128 to linear movement of slider 150 along shaft 154 and the longitudinal axis of housing 120. Since collar 152 is coupled to slider 150 and mounted over shaft 154, collar 152 moves with slider 150 in the longitudinal direction. Collar 152 is also mounted to a proximal end of the resilient member. Therefore, the user can translate the resilient member in the longitudinal direction to deflect the distal end of inner elongated member 34 and outer elongated member 22 by rotating external cylinder 128 a desired angular magnitude. In addition, external cylinder 128 may keep the deflection of the inner elongated member 34 when the user releases contact with the external cylinder 128. The pitch of threaded structures 146 and 148 may be selected to balance ease of rotation of external cylinder 128 and minimizing the amount of rotation required to deflect the distal end of inner elongated member 34. Shaft 152 also couples to wheel 126 such that rotation of wheel 126 of the rotation control mechanism also causes shaft 154 and collar 152 to rotate at an equal angular velocity.

FIG. 9B illustrates another view of the deflection control mechanism for housing 120. Collar 152 defines an aperture through which shaft 154 can be disposed. In addition, collar 152 defines a channel extending radially outward from the aperture and configured to accept rib 160 of shaft 154 that prevents rotation of collar 152 with respect to shaft 154.

Collar 152 also defines a mounting hole 162. The resilient member may be threaded through mounting hole 162 and fixed to collar 162 via crimping of a hypotube or other fixing method.

Figure 10A:
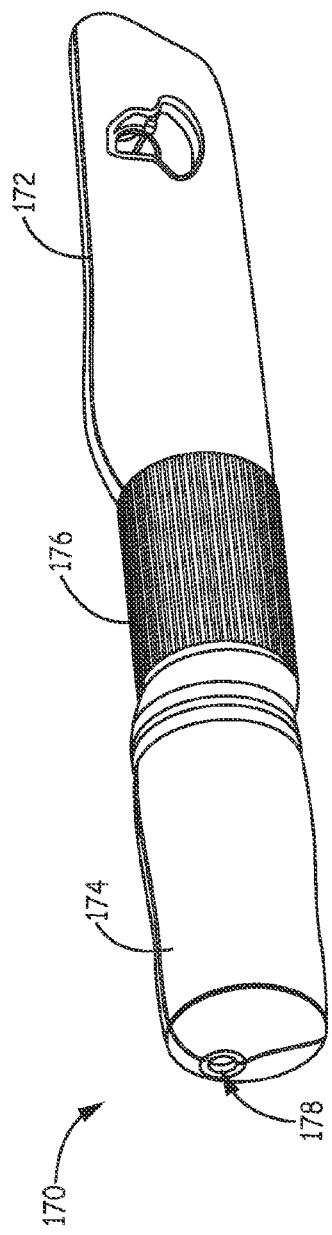
FIG. 10A is a perspective view of an example housing of a delivery system.

FIG. 10A is a perspective view of an example housing 170 of a delivery system similar to delivery system 10. Housing 170 may be similar to housing 120 described above. However, housing 170 may include a rotation control mechanism and a deployment mechanism that varies from housing 120. Housing 170 may define an opening 178 through which inner elongated member 34 and, in some example, outer elongated member 22 may enter housing 170. Housing 170 may also be coupled to slider external cylinder 174 of the deployment mechanism and the rotation control mechanism and exterior cylinder 176 of the deflection control mechanism. In this manner, external cylinder 174 may be the control input for both the deployment mechanism for outer elongated member 22 withdrawal and rotation of inner elongated member 22. The entire external cylinders 174 and 176 may independently rotate about housing 170. However, only a partial circumference of external cylinders 174 and/or 176 may be exposed external from housing 170 in other examples. Housing 170 may also define handle 172.

Figure 10B:
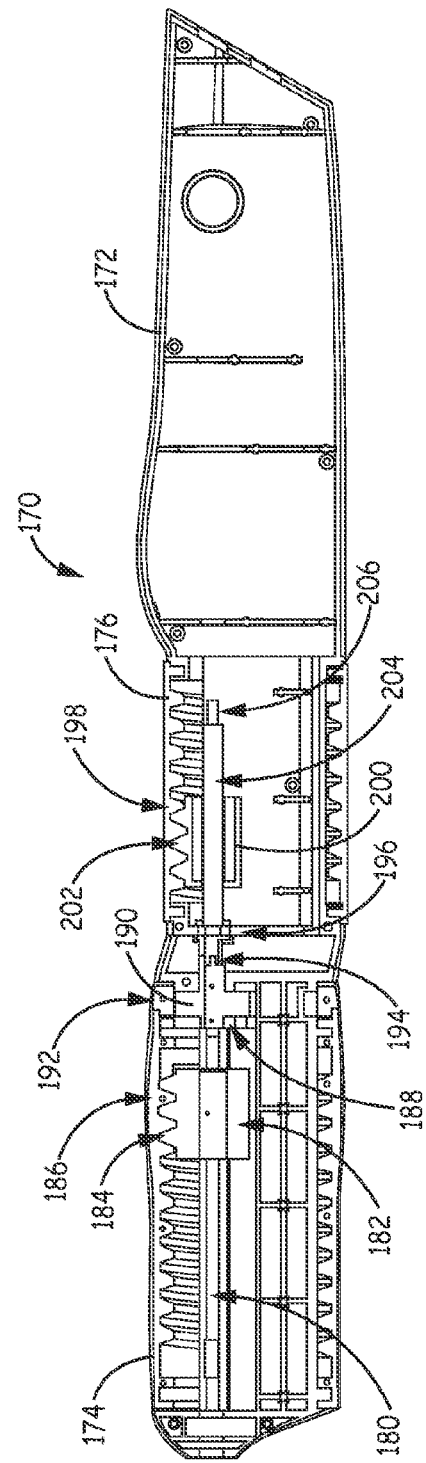
FIG. 10B is a cross-sectional view of the housing of the delivery system of FIG. 10A.

The components associated with housing 170 as described in FIGS. 10A, 10B, 10A, and 10B are examples of components that may achieve the functionality described herein. Therefore, some components may be altered to achieve different shapes or dimensions while still maintaining the functionality described herein with respect to the deployment mechanism, the rotation control mechanism, and the deflection control mechanism FIG. 10B is a cross-sectional view of housing 170 of the delivery system of FIG. 10A. As discussed above, housing 170 may be similar to housing 120 described above and include some similar components. For example, external cylinder 176 and the deflection mechanism may be substantially similar to external cylinder 128 and the deflection mechanism of housing 120 in FIG. 8B. However, housing 170 includes a different deployment mechanism and rotation control mechanism. Specifically, the deployment mechanism for withdrawing the outer elongated member 22 with respect to inner elongated member 34 and the rotation control mechanism are combined into a common mechanism.

As shown in FIG. 10B, the rotation control mechanism and deployment mechanism includes external cylinder 174 at least partially external of housing 170. External cylinder 174 may include threaded structure 186 on an inner surface of external cylinder 174 at a distal portion of the external cylinder 186 and a planetary gear surface 192 at a proximal portion of external cylinder 174. In this manner, rotation of external cylinder 174 rotates both of threaded structure 186 and planetary gear surface 192 at the same time.

Slider 182 is disposed internal of external cylinder 174 and configured to move along the longitudinal axis defined by track 180 in housing 170. Slider 182 may also include an inner cylinder defining an aperture 210 through which inner elongated member 34 is disposed, and slider 182 is coupled to a proximal end of outer elongated member 22. Slider 182 may also include at least one ridge 208 (shown in FIG. 11A) running longitudinally along an external surface of the cylinder of slider 182, the at least one ridge 208 configured to mate with a respective track defined by housing 170. Slider 182 may also include threaded structure 184 configured to mate with threaded structure 186 of external cylinder 174. In this manner, rotation of external cylinder 174 by a user causes linear movement of slider 182 along the longitudinal axis of housing 170.

Housing 170 is also coupled to sun gear 190 that is configured to mate with planetary gear surface 192 of external cylinder 174. Sun gear 190 is also coupled to support 188 defined by housing 170. Sun gear 190 is attached to and concentric with a portion of inner elongated member 34, and sun gear 190 is also coupled to a distal end of shaft 206 via connection interface 194. In this manner, user rotation of external cylinder 174 causes longitudinal movement of internal slider 182 and outer elongated member 22 simultaneous with rotation of sun gear 190, inner elongated member 34, shaft 204, and collar 200.

Simultaneous operation of the deployment mechanism and the rotation control mechanism may simplify the process of rotating IMD 26 and withdrawing outer elongated member 22 at the correct time. For example, from the fully extended position of outer elongated member 22, rotation of external cylinder 174 may initially begin withdrawing the distal end 24 of outer elongated member 22 before helical fixation element 28 is exposed. The user may even place the distal end 24 against the target tissue location 38 as outer elongated member 22 is withdrawn. During rotation of external cylinder 174, inner elongated member 34 is always rotating. Once the distal tip of helical fixation element 28 emerges distally from distal end 24 of outer elongated member 22, rotation of helical fixation element 28 causes the helical fixation element to pierce tissue and begin insertion into the tissue.

The user may continue rotating external cylinder 174 until helical fixation element 28 is fully inserted into the tissue. In some examples, threaded structures 186, 184 may be configured with a pitch such that slider 182 contacts a proximal surface of housing 170 when outer elongated member becomes fully withdrawn from IMD 26. Similarly, the gear ratio and distances between planetary gear surface 192 and sun gear 190 may be selected such that slider 182 contacts the proximal surface of housing 170 when sun gear 190 has rotated IMD 26 the same number of revolutions as the number of rotations in helical fixation element 28. In other words, the pitches of the threaded surfaces 186, 184 may be selected to match the gear ratio between planetary gear surface 192 and sun gear 190 such that both the withdrawal of outer elongated member 22 and the insertion of helical fixation element 28 complete at the same time. However, such synchronicity may not be utilized in each example of housing 170.

The deflection control mechanism of housing 170 may be substantially similar to the deflection control mechanism of housing 120 of FIG. 8B. The deflection control mechanism of housing 170 in FIG. 10B includes external cylinder 176, slider 200, shaft 204, and collar 224 (shown in FIG. 11B). External cylinder 176 is at least partially external of housing 170, and external cylinder 176 includes a threaded structure 198 on an internal surface of the external cylinder.

Slider 200 is configured to move along the longitudinal axis of housing 170. Housing 170 also defines a track (not shown) that engages with an outer surface of slider 200 to retain slider 200 along a liner path within housing 170. Slider 200 also defines a cylinder having an aperture, and at least one ridge 222, or rib, running longitudinally along an external surface of the cylinder of slider 200. Ridge 222 (shown in FIG. 11B) may be configured to mate with a track defined by housing 170. Slider 200 may also include a threaded structure 202 configured to mate with threaded structure 198 of external cylinder 176. In this manner rotation of external cylinder 176 causes linear movement of slider 200 along the longitudinal axis and shaft 204.

Shaft 204 comprises at least one rib 226 (shown in FIG. 11B) extending longitudinally along an exterior surface of shaft 204, wherein at least a portion of shaft 204 is disposed within the cylinder defined by slider 200. Shaft 204 may also include mounting member 206 that mates to a retainer defined by housing 170 and configured to allow shaft 204 to rotate about the longitudinal axis and prevent shaft 204 from moving axially along the longitudinal axis. Shaft 204 may also contact housing 170 at retainer 196.

Collar 224 (shown in FIG. 11B) defines an aperture, at least one channel extending radially outward from the aperture and longitudinally along collar 224, and a mounting hole configured to mount the proximal end of the resilient member (e.g., a pull-wire). The at least one channel is configured to mate with the at least one rib 226 of shaft 204. In addition, at least a portion of collar 224 is disposed between the cylinder of slider 200 and shaft 204 such that collar 224 can rotate within the cylinder of slider 200 and slide longitudinally along shaft 204. Therefore, user rotation of external cylinder 176 with respect to housing 170 causes longitudinal displacement of collar 224 and the resilient member. Although not explicitly shown, housing 170 defines structures required to mount each component of the deployment mechanism, rotation control mechanism, and deflection control mechanism within housing 170.

Figure 11A:
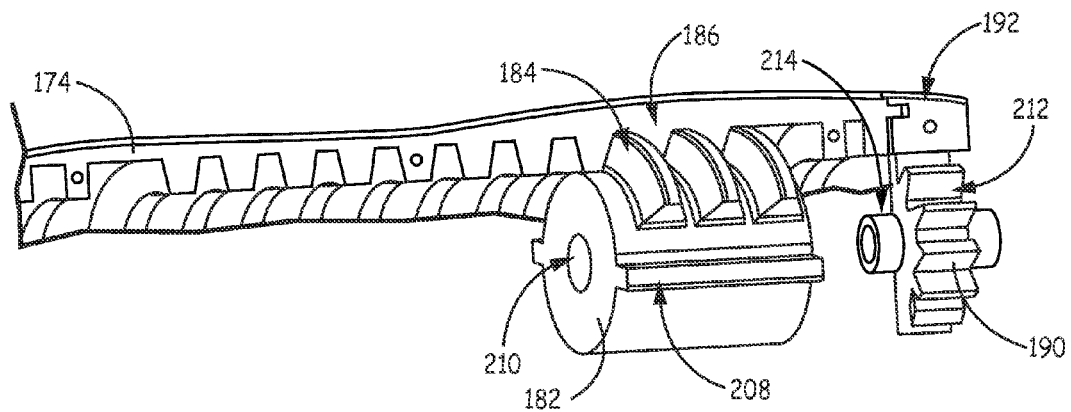
FIG. 11A is a perspective view of a second external cylinder, a second slider, and a sun gear of an example rotation control mechanism of the delivery system of FIG. 10A.

FIG. 11A is a perspective view of external cylinder 174, slider 182, and sun gear 190 of an example rotation control mechanism 180 of the delivery system of FIG. 10A. As shown in FIG. 11A, external cylinder 174 is only partially shown. Slider 182 includes ridges 208 running along a longitudinal external surface of slider 182 such that ridges 208 can mate to respective tracks within housing 170 (not shown). Slider 182 also defines aperture 210 configured to surround inner elongated member 34. Aperture 210 may also accept a proximal end of outer elongated member 22 such that slider 182 can be fixed to the outer elongated member. Sun gear 190 includes teeth 212 and axle 214. Axle 214 may be configured to rest within support 188 of housing 170 that retains sun gear 190 in the appropriate longitudinal position. Teeth 212 are configured to mate with teeth (not shown) of planetary gear surface 192 defined by exterior cylinder 174.

Figure 11B:
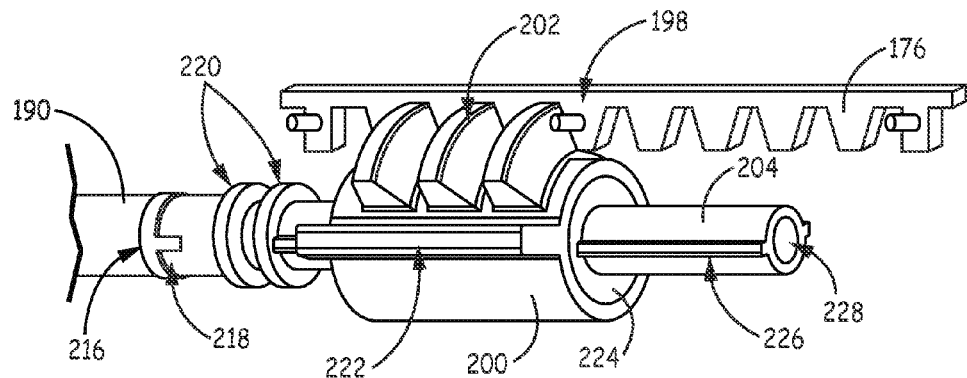
FIG. 11B is a perspective view of a first external cylinder, a first slider, a shaft, and a collar of an example deflection control mechanism of the delivery system of FIG. 10A.

FIG. 11B is a perspective view of external cylinder 176, slider 200, shaft 204, and collar 224 of an example deflection control mechanism of the delivery system of FIG. 10A. As shown in FIG. 11B, only a portion of external cylinder 176 is shown to illustrate other components. Shaft 204 includes ribs 226 and defines a lumen 228. Lumen 228 may provide access to a lumen of inner elongated member 34. Ribs 226 are configured to mate with channels defined by collar 224 to allow collar 224 to slide along shaft 204 and prevent rotation of collar 224 with respect to shaft 204. Ridges 222 of slider 200 allow slider 200 to move longitudinally within housing 170 and prevent rotation of slider 200 with respect to housing 170.

Shaft 204 may also include flanges 220 configured to reside on either side of a retainer 196 (shown in FIG. 10B) of housing 170. Connection interface 194 (shown in FIG. 10B) may be made of distal end 218 of shaft 204 and proximal end 216 of sun gear 190. In this manner, distal end 218 may mate with proximal end 216 such that rotation of sun gear 190 causes equal angular rotation of shaft 204, collar 224, and the resilient member attached to collar 224.

Figure 12:
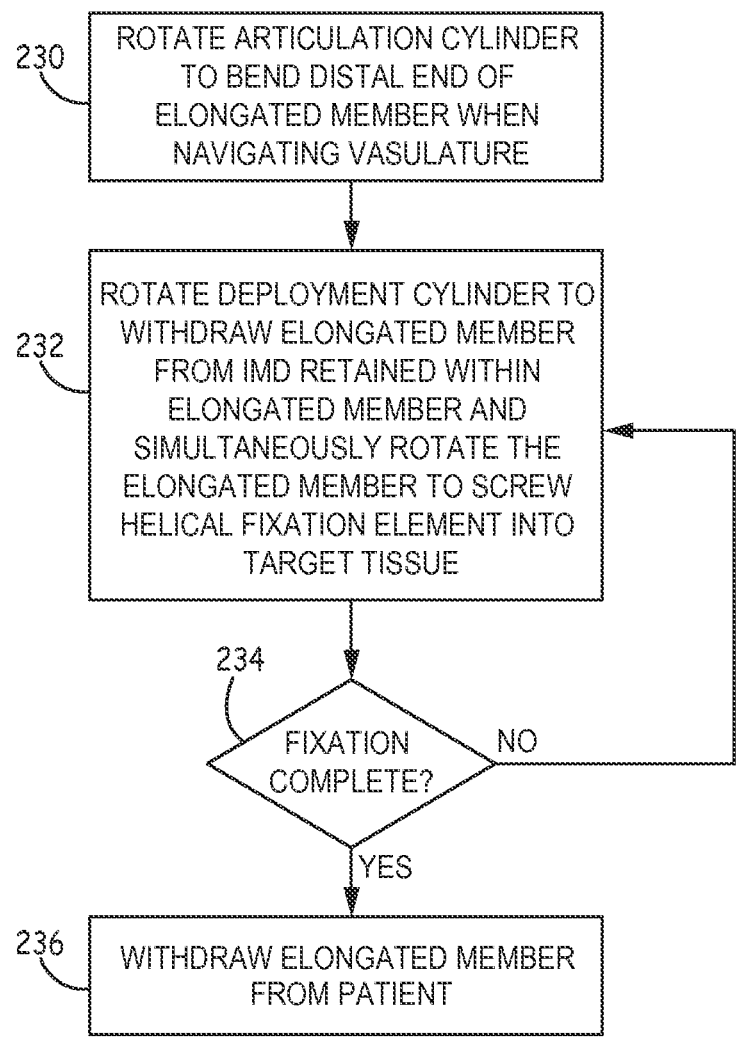
FIG. 12 is a flow diagram illustrating an example process for operating the delivery system of FIG. 10A.

FIG. 12 is a flow diagram illustrating an example process for operating the delivery system and housing 170 of FIG. 10A. As shown in FIG. 12, a user may rotate an articulation cylinder (e.g., exterior cylinder 176 to bend, or articulate, the distal end of the inner elongated member 34, and outer elongated member 22, when navigating through patient vasculature or other anatomical structures (230). Once IMD 26 is located adjacent to target tissue location 38, the user may start to implant IMD 26. The user rotates the deployment cylinder (e.g., external cylinder 174) to withdraw the outer elongated member 22 from IMD 26 retained within distal end 24 of the outer elongated member and simultaneously rotate inner elongated member 34 to screw helical fixation element into target tissue (232).

If fixation is not yet complete ("NO" branch of block 234), the user may continue to rotate deployment cylinder (e.g., external cylinder 174) (232). If fixation of helical fixation element 28 is complete ("YES" branch of block 234), IMD 26 is fixed to the tissue via helical fixation element 28 and the user may withdraw the inner and outer elongated members from the patient (236). In some examples, the user may need to release a tether that couples IMD 26 to inner elongated member 34.

In some examples, the delivery system of housing 170 may be used to retrieve IMD 26 after the IMD has been implanted. In this manner, the process for retrieval of IMD 26 of FIG. 12 may be reversed. In addition, or in other examples, a tether may be used to attach to IMD 26 and remove IMD 26 from the target tissue location 38.

Figure 13A:
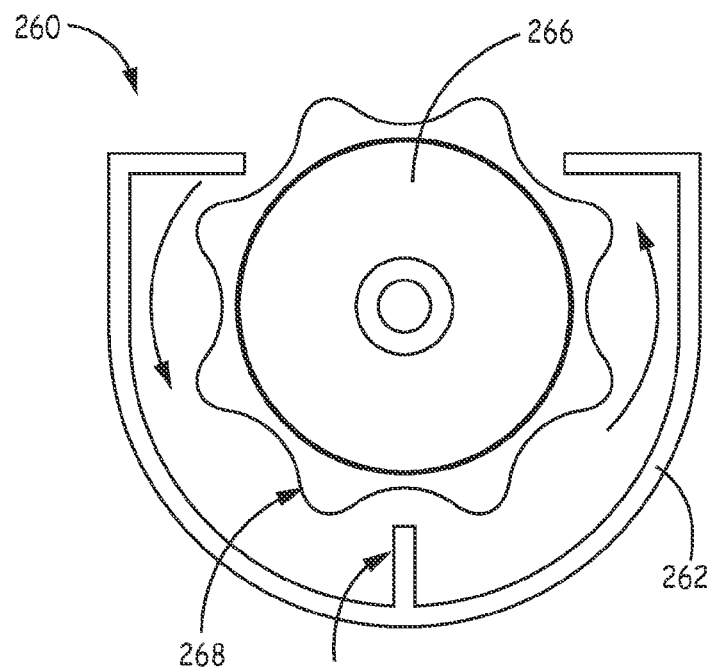
FIGS. 13A and 13B are conceptual diagrams illustrating example mechanisms for controlling an amount of rotational displacement of an elongated member and an IMD during operation of a delivery system.
Figure 13B:
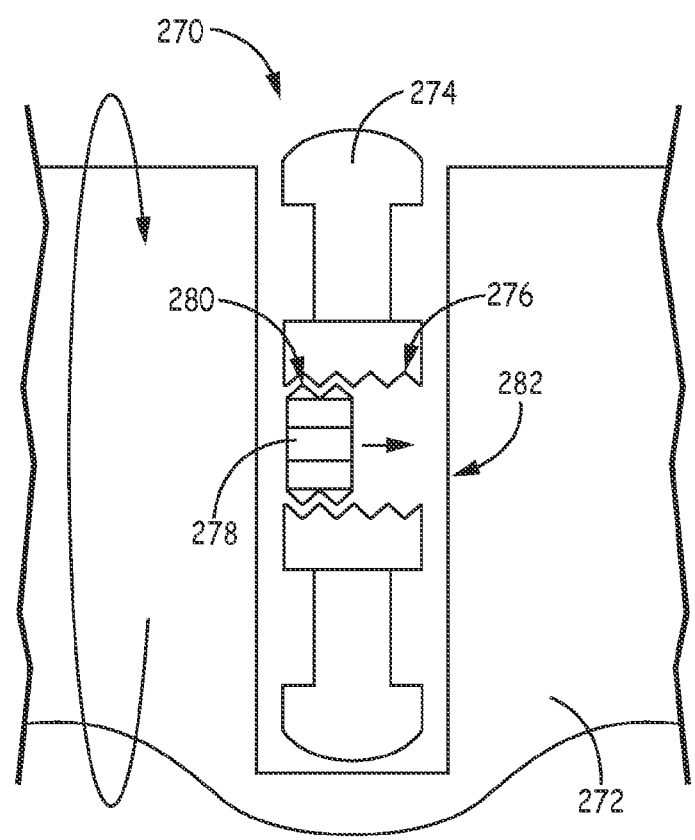

FIGS. 13A and 13B are conceptual diagrams illustrating example mechanisms for controlling an amount of rotational displacement of an inner elongated member 34 and an IMD 26 during operation of a delivery system. As a user manipulates a rotation control mechanism, the user may benefit from receiving feedback regarding the amount of rotation applied to helical fixation element 28 of IMD 26 or even a mechanical limiter that prevents over-rotation, and over-insertion, of helical fixation element 28.

As shown in FIG. 13A, rotation feedback mechanism 260 includes a wheel 266 (e.g., wheel 18 or wheel 126) of a rotation control mechanism for applying rotational torque to helical fixation element 28. Wheel 266 may include protrusions 268 alternating with depressions along an outer surface of wheel 266. Housing 262 may be similar to housing 12 or 120. In addition, housing 262 may include a rib 264 that extends inwards towards wheel 266. As the user rotates the rotation control mechanism and wheel 266, protrusions 268 cause periodic contact episodes between the protrusions 268 and the rib 264.

Each contact episode may signal an amount of rotational displacement of the inner elongated member 34 and IMD 26 and helical fixation element 28. For example, a contact episode may generate an audible "click" that can be heard by the user of the device. In addition, or alternatively, each contact episode may provide tactile feedback that another amount of angular rotation has been applied. In this manner, the user may know the angular rotation for each contact episode (e.g., generally between 10 degrees and 90 degrees), or the number of contact episodes for a full rotation of 360 degrees. In some examples, the user may know number of contact episodes required to fully insert helical fixation element 28 such that a distal end of the housing of IMD 26 contacts the tissue (e.g., ten contact episodes equals full insertion). The rotation feedback mechanism 260 may be applied to any of the rotation components described herein. In addition, other structures may be used to provide similar contact episodes for feedback as to the progress of fixation of IMD 26.

As shown in FIG. 13B, rotation limit mechanism 270 may physically prevent a user from over-rotating and overinserting helical fixation element into tissue. For example, a rotation control mechanism may be coupled to rotation limit mechanism 270. Wheel 274 may be similar to wheels 18 or 126 described herein. Wheel 274 may define threaded structure 276 disposed on an inner surface of a channel within wheel 274. Rotation limiting structure 278 may be disposed within the channel and coupled to wheel 274 of the rotation control mechanism via mating threaded structure 280.

Rotation limiting structure 278 may also include rails that contact tracks within housing 272 that allow rotation limiting structure 278 to slide longitudinally without rotating with respect to housing 272. In this manner, rotation or manipulation of wheel 274 may cause rotation limiting structure 278 to move linearly towards stop portion 282 of housing 272. After wheel 274 rotates a predetermined number of revolutions (e.g., the number of revolutions needed to rotate inner elongated member 34 and helical fixation element 28 for proper fixation), rotation limiting structure 278 may be configured to contact stop portion 282 of housing 272. Once rotation limiting structure 278 contacts stop portion 282, wheel 274 may no longer be able to rotate in that direction. In this manner, threaded structures 276 and 280 may be selected with a pitch that allows wheel 274 to rotate the required number of revolutions and causes rotation limiting structure 278 to stop wheel 274 when the required number of revolutions have occurred. In addition, the distance between rotation limiting structure 278 and stop portion 282 may similar be selected to allow the appropriate number of revolutions for insertion of helical fixation element 28 into tissue. Other types of rotation limiting structures may similarly be implemented to reduce the likelihood of over-insertion of helical fixation element 28.

FIGS. 14A-14J are conceptual diagrams illustrating examples of different keyed surface at a distal end of an elongated member 34 for mating with a keyed structure 29 of IMD 26. Inner elongated member 34 may include a keyed surface (e.g., keyed surface 244 of FIGS. 14A and 14B or 254 of FIGS. 14C and 14D) at the distal end of the elongated member. The keyed surface is configured to mate with a keyed structure 29 defined by IMD 26 to translate rotational force (e.g., torque) from inner elongated member 34 to IMD 26 and helical fixation element 28. Any type of keyed structure may be sufficient to translate torque from inner elongated member 34 to IMD 26.

Figure 14A:
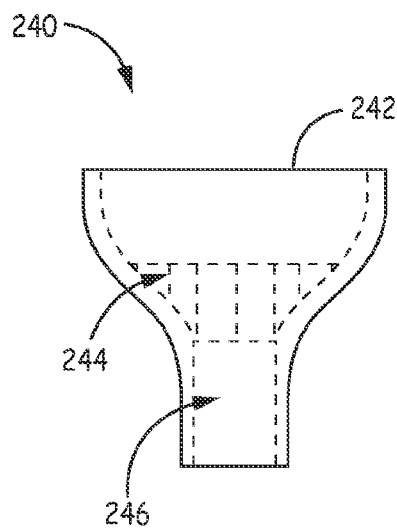
FIGS. 14A-14J are conceptual diagrams illustrating example keyed surface at a distal end of an elongated member for mating with a keyed structure of an IMD.
Figure 14B:
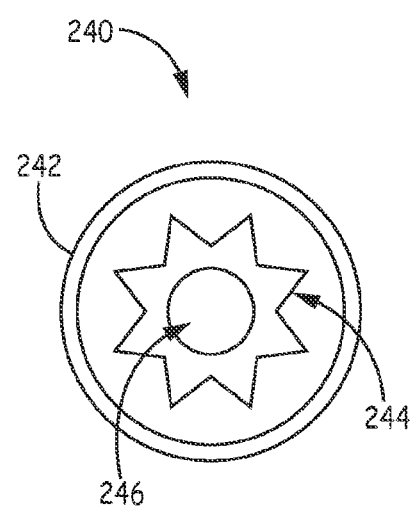

As shown in the side view of FIG. 14A and the top view of 14B, example keyed mechanism 240 includes distal end 242 of inner elongated member 34. Distal end 242 may accept matching keyed structure 29 of IMD 26. Keyed structure 244 is shown as a star pattern with eight points. Therefore, keyed structure 29 of IMD 26 may include a similar eight point star pattern. However, other star patterns may include fewer points or a greater number of points. A greater number of points in the star pattern may increase the number of acceptable circumferential orientations at which the keyed structure of IMD 26 can fit into keyed structure 244. Lumen 246 may be defined by inner elongated member 34.

Figure 14C:
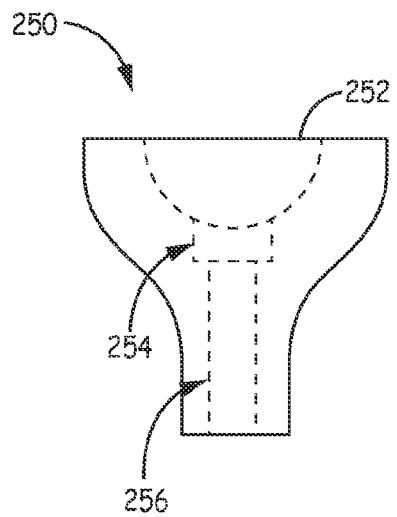
Figure 14D:
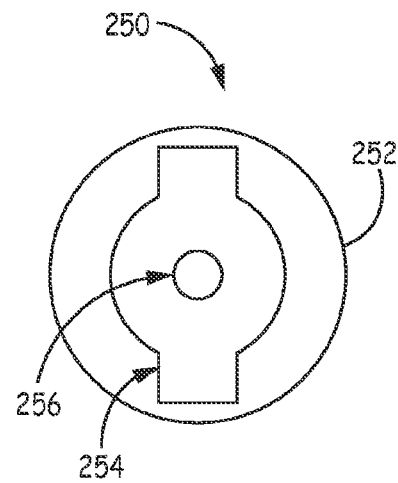

As shown in the side view of FIG. 14C and the top view of 14D, example, keyed mechanism 250 includes distal end 252 of inner elongated member 34. Distal end 252 may accept matching keyed structure 29 of IMD 26. Keyed structure 254 is shown as including opposing channels. Therefore, keyed structure 29 of IMD 26 may include a similar pair of opposing flanges that mate with the opposing channels of keyed structure 254. Lumen 256 may be defined by inner elongated member 34.

Figures 14E, 14F:
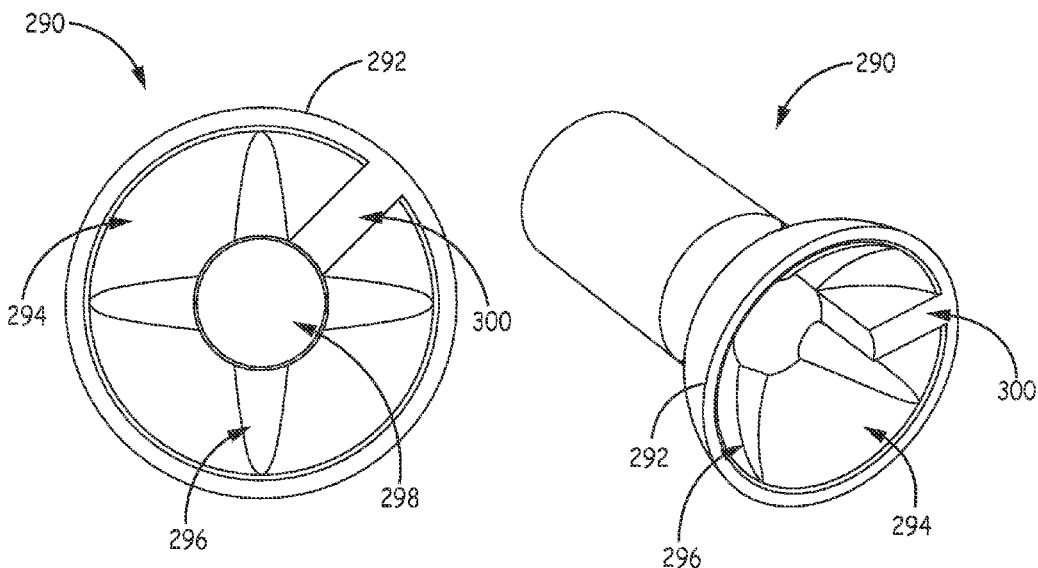

As shown in the top view of FIG. 14E and the perspective view of FIG. 14F, example, keyed mechanism 290 includes distal end 292 of inner elongated member 34. Distal end 292 may accept matching keyed structure 29 of IMD 26. Keyed mechanism 290 may include multiple (e.g., four) depressions 296 in cup surface 294 and a single protrusion 300 at a circumferential position within keyed mechanism 290. Therefore, keyed structure 29 of IMD 26 may include ridges that mate to respective depressions 296 and a slot configured to mate with protrusion 300. In this manner torque may be transferred from keyed mechanism 290 to keyed structure 29 of IMD 26 via depressions 296 and/or protrusion 300. Although four depressions 296 are shown, fewer or greater number of depressions may be used in other examples. In some examples, keyed mechanism 290 may only include depressions 296 or protrusion 300. Lumen 298 may be defined by inner elongated member 34.

Figures 14G, 14H:
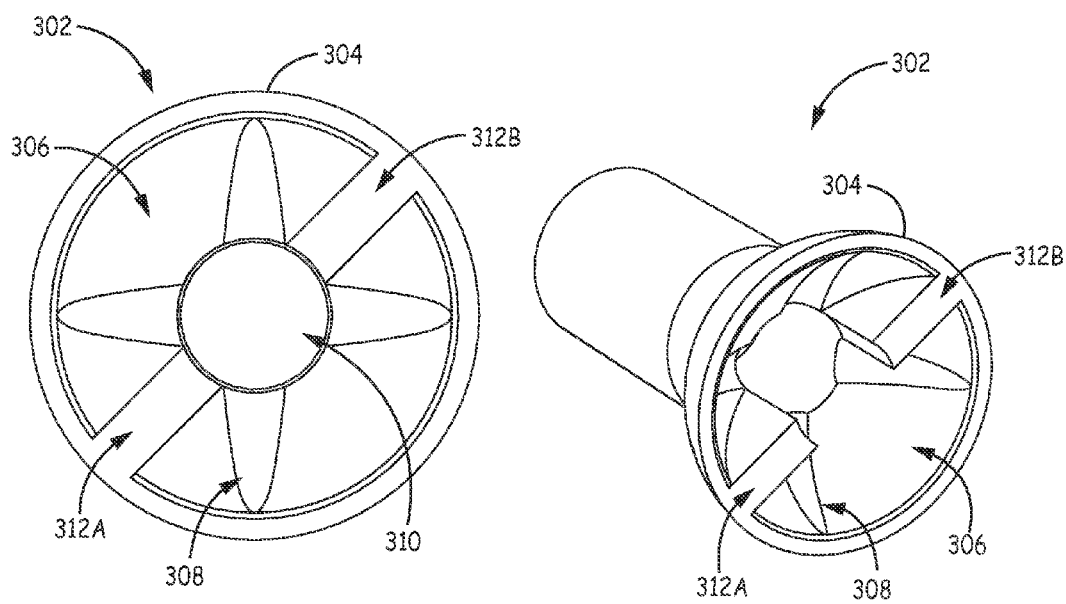

As shown in the top view of FIG. 14G and the perspective view of FIG. 14H, example, keyed mechanism 302 includes distal end 304 of inner elongated member 34. Keyed mechanism 302 may be substantially similar to keyed mechanism 290 of FIGS. 14E and 14F, except that keyed mechanism 302 includes two opposing protrusions 312A and 312B (collectively "protrusions 312"). Distal end 304 may accept matching keyed structure 29 of IMD 26. Keyed mechanism 302 may include multiple (e.g., four) depressions 308 in cup surface 306 and a two protrusions 312 at respective circumferential positions within keyed mechanism 302. Therefore, keyed structure 29 of IMD 26 may include ridges that mate to respective depressions 308 and slots configured to mate with protrusions 312. In this manner torque may be transferred from keyed mechanism 302 to keyed structure 29 of IMD 26 via depressions 308 and/or protrusions 312. Lumen 298 may be defined by inner elongated member 34.

Figure 14I:
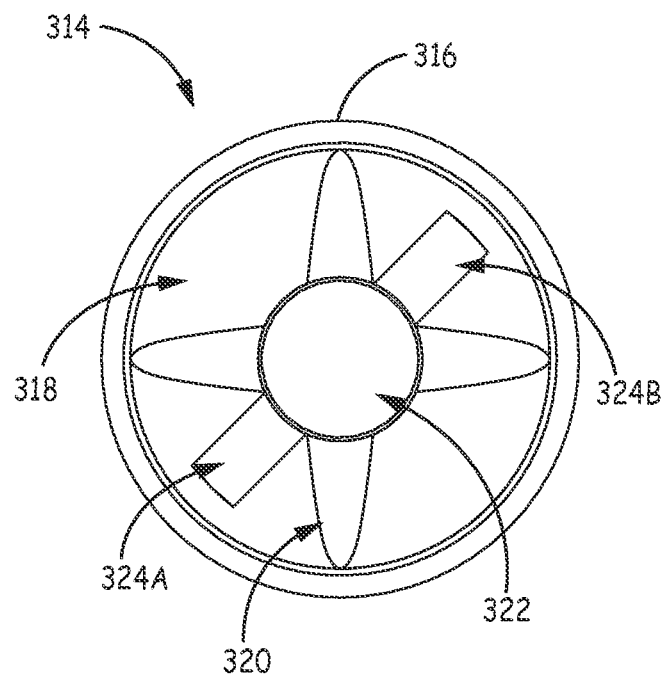
Figure 14J:
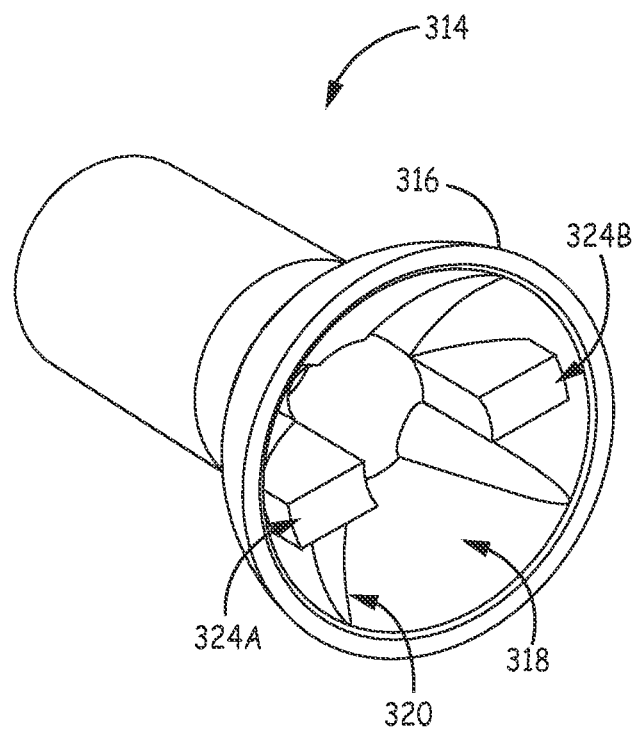

As shown in the top view of FIG. 14I and the perspective view of FIG. 14J, example, keyed mechanism 314 includes distal end 316 of inner elongated member 34. Keyed mechanism 314 may be substantially similar to keyed mechanism 302 of FIGS. 14G and 14H, except that keyed mechanism 314 includes two opposing protrusions 324A and 324B (collectively "protrusions 324") that do not extend to the side of distal end 316. Distal end 316 may accept matching keyed structure 29 of IMD 26. Keyed mechanism 316 may include multiple (e.g., four) depressions 320 in cup surface 306 and a two protrusions 324 at respective circumferential positions within keyed mechanism 316. However, both protrusions 324 do not extend radially all the way to the edge of distal end 316. Instead, each protrusion 324 forms a gap between the distal end 316 and the edge of the respective protrusion. Keyed structure 29 of IMD 26 may include ridges that mate to respective depressions 320 and slots configured to mate with protrusions 324. In this manner torque may be transferred from keyed mechanism 314 to keyed structure 29 of IMD 26 via depressions 320 and/or protrusions 324. Lumen 322 may be defined by inner elongated member 34.

FIGS. 15A-15E are conceptual diagrams illustrating an example cup surface 332 at a distal end of an elongated member 34 for friction fit mating with a proximal structure of IMD 26. A tether (e.g., a thread or cable) may be disposed within inner elongated member 34 and interact with the proximal structure of IMD 26. For example, the tether may loop through a hole defined by the proximal structure, clamp to the proximal structure, or otherwise temporarily attach to the proximal structure of IMD 26. In other examples, a mechanical attachment release mechanism may be used instead of a tether. The delivery system (e.g., delivery system 10) may include a tether tension mechanism configured to apply tension to the tether and pull the proximal structure of IMD 26 and/or a proximal surface of the housing of IMD 26 in contact with cup surface 332. The tether may then be locked to the handle of delivery system 10, for example, for attachment of IMD 26 to tissue and released to allow IMD 26 to remain within the patient. In this manner, a frictional fit may be formed between cup surface 332 and IMD 26 that enables the transfer of torque between inner elongated member 34 and IMD 26.

Figure 15A:
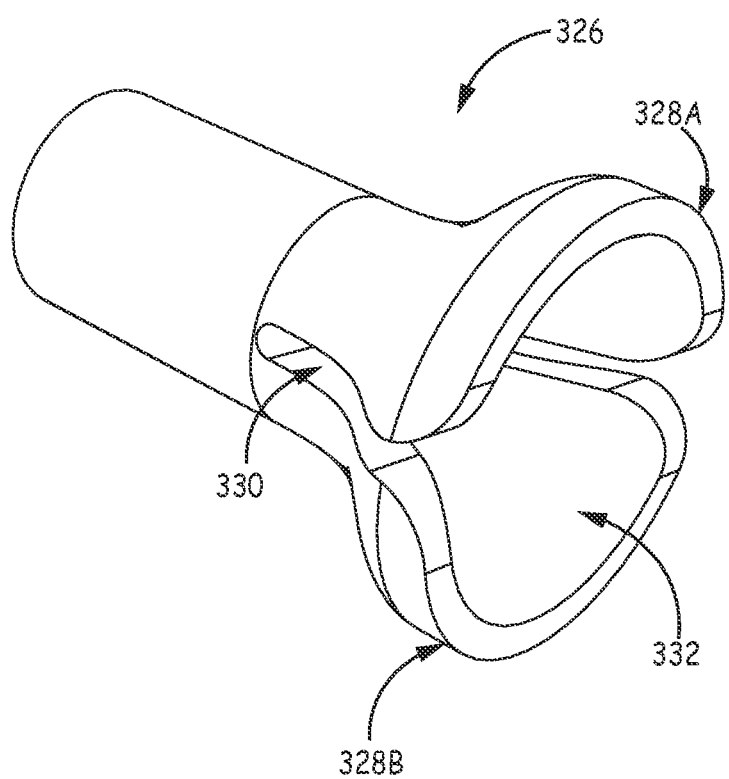
FIGS. 15A-15E are conceptual diagrams illustrating an example cup surface at a distal end of an elongated member for friction fit mating with a structure of an IMD.

As shown in FIG. 15A, cup structure 326 is located at the distal end of inner elongated member 34 and is formed by opposing curved flanges 328A and 328B (collectively "curved flanges 328"). Curved flanges 328 define slot 330 located between each of the curved flanges. Together, curved flanges 328 form cup surface 332 which may be conically shaped in some examples. When the proximal structure of IMD 26 is pulled into curved flanges 328, the force may cause the curved flanges 328 to bias slightly outward. This bias may promote the frictional fit between cup surface 332 and IMD 26. However, in some examples, curved flanges 328 may not flex due to the force from IMD 26. Cup surface 332 may be smooth or formed with a texture that may promote friction with the proximal structure of the IMD. Cup structure 326 may be constructed of one or more polymers, composite materials, and/or metal alloys. Materials may be selected to achieve desired flexibility or rigidity of the structures. Typically, the materials may be biocompatible as well. Side view FIG. 15B and top view FIG. 15C illustrates the various features of cup structure 326 such as curved flanges 328, cup surface 332, and lumen 334 formed by inner elongated member 34. Slots 330A and 330B are on opposing sides of lumen 334 and may allow for deflection and bias of curved flanges 328.

Figure 15B:
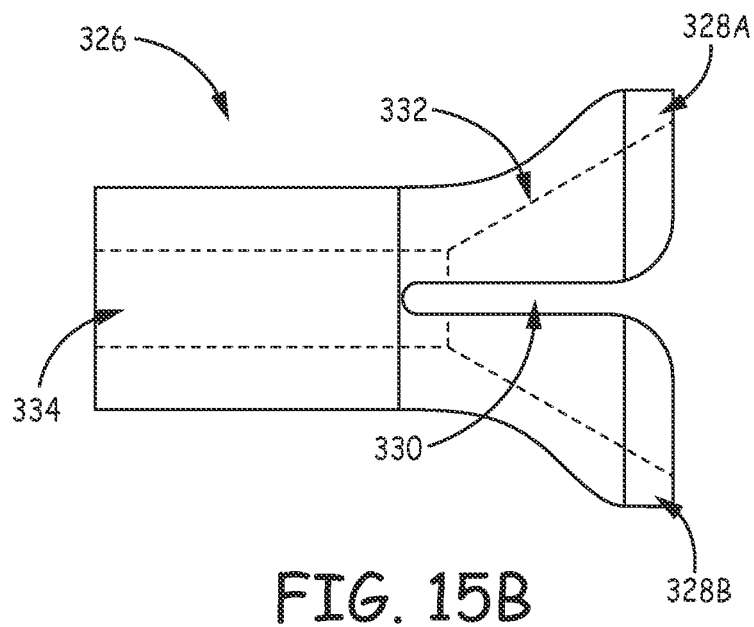
Figure 15C:
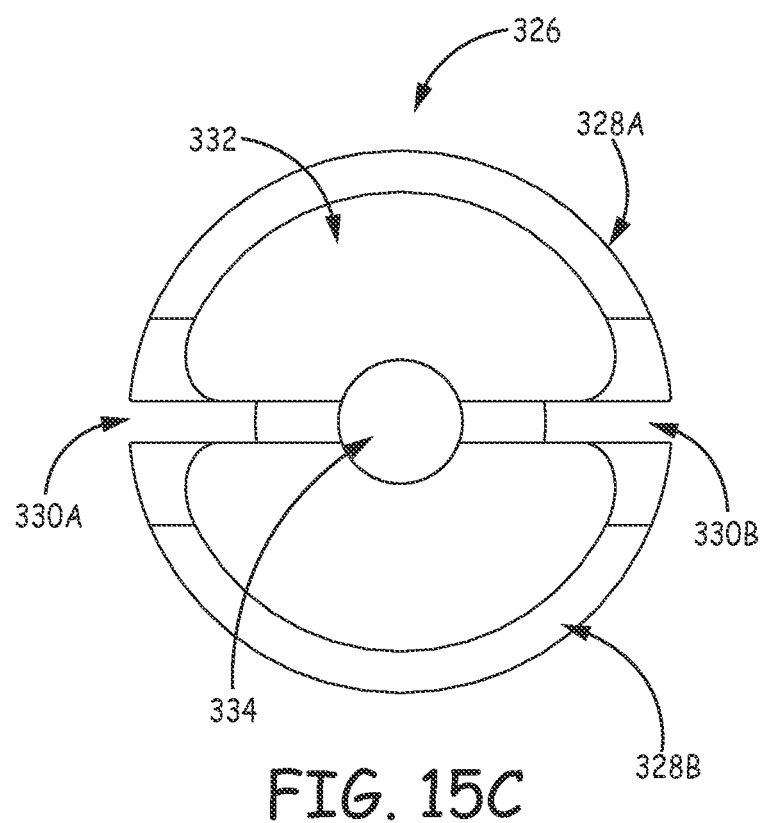
Figure 15D:
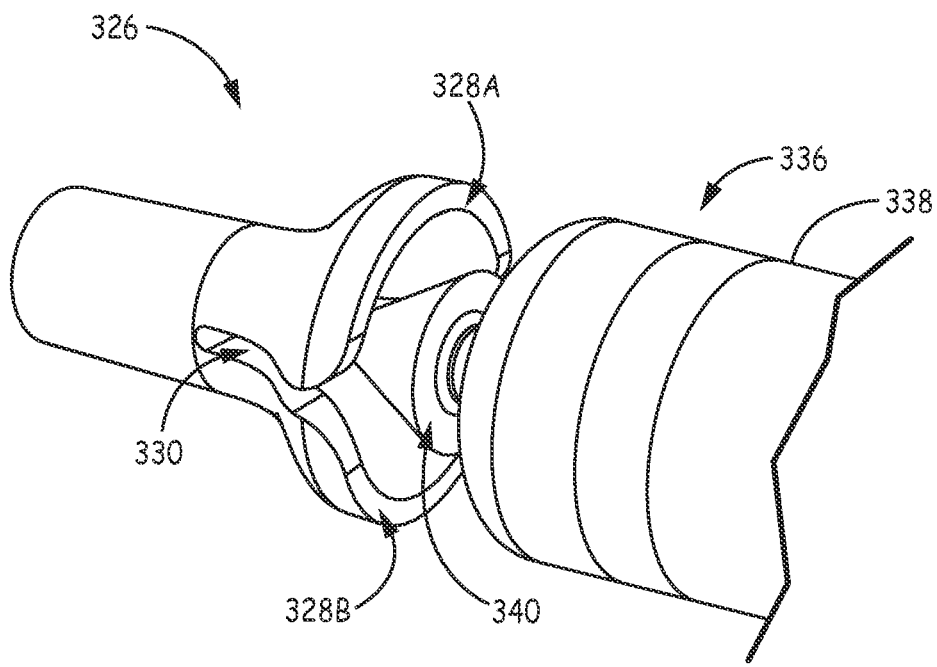
Figure 15E:
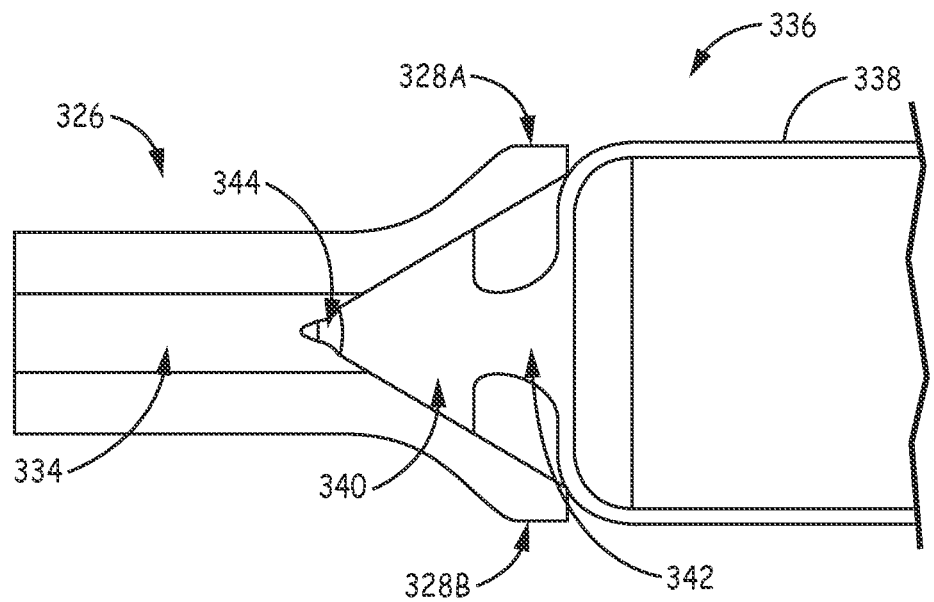

FIG. 15D is a perspective view and FIG. 15E is a cross-sectional view of the mating between cup structure 326 of FIGS. 15A-15C and proximal structure 340 of IMD 336. IMD 336 may be similar to IMD 26. IMD 336 also includes housing 338 to which proximal structure 340 is attached or formed with via neck 342. Proximal structure 340 also defines tether hole 344 through which a tether may be threaded. FIG. 15D shows proximal structure 340 within cup structure 326 but not yet contacting cup surface 332. FIG. 15E shows when proximal structure 340 is in contact with cup surface 332 of cup structure 326. A portion of proximal structure 340 may be disposed within lumen 334. Cup structure 326 is shown as contacting the proximal end of housing 338, but cup structure 326 may not contact housing 338 in other examples. In some examples, neck 342 may allow a retrieval loop to grasp IMD 336 and retrieve IMD 336 from the patient. In some examples, the retrieval loop may also be used to pull IMD 336 towards cup structure 326 and rotate IMD 336 via the frictional fit.

FIGS. 16A-16E are conceptual diagrams illustrating an example cup surface 356 with circumferential ridges at a distal end of an elongated member 34 for friction fit mating with a structure of an IMD 26. Cup structure 350 may be substantially similar to cup structure 326 of FIGS. 15A-15E. However, cup surface 356 includes circumferential ridges lining the inside of curved flanges 352A and 352B (collectively "curved flanges 352"). The circumferential ridges may be configured to mate with corresponding circumferential ridges on the proximal structure of the IMD or even a smooth surface on the proximal structure of the IMD. Curved flanges 352 define slot 354 located between each of the curved flanges. Together, curved flanges 352 form cup surface 356 which may be conically shaped in some examples.

Figure 16A:
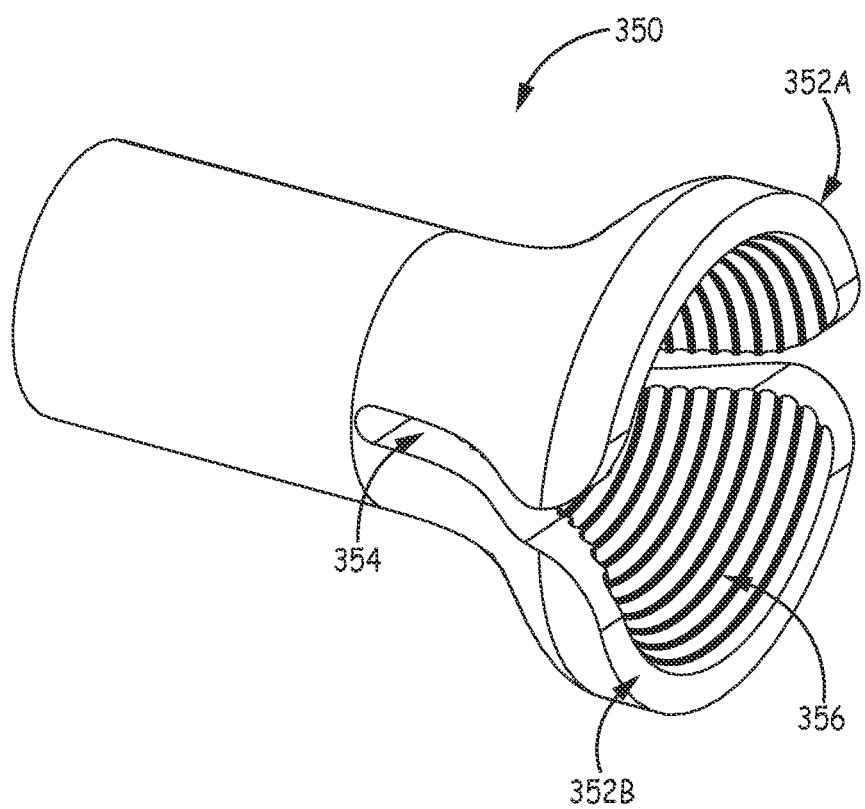
FIGS. 16A-16E are conceptual diagrams illustrating an example cup surface with circumferential ridges at a distal end of an elongated member for friction fit mating with a structure of an IMD.
Figure 16B:
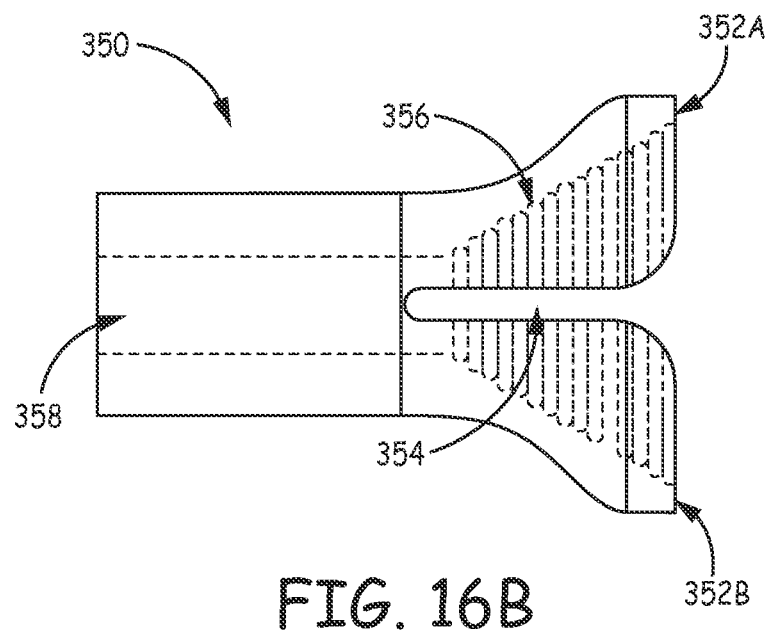
Figure 16C:
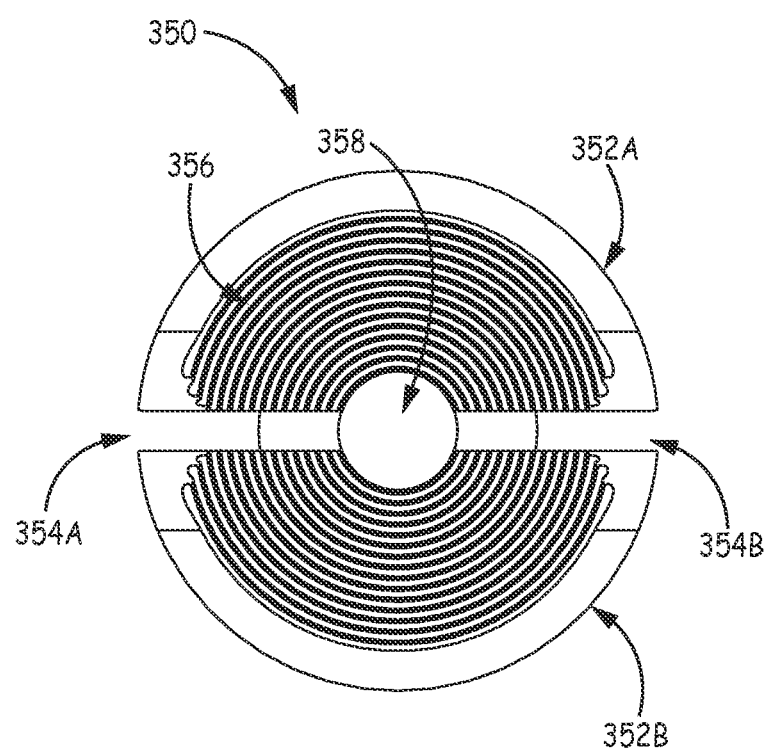

Side view FIG. 16B and top view FIG. 16C illustrates the various features of cup structure 350 such as curved flanges 352, cup surface 356, and lumen 358 formed by inner elongated member 34. Slots 354A and 354B are on opposing sides of lumen 358 and may allow for deflection and bias of curved flanges 352. When viewed from the top, the circumferential ridges forming cup surface 356 may appear like concentric circles positioned along the curved flanges 352.

Figure 16D:
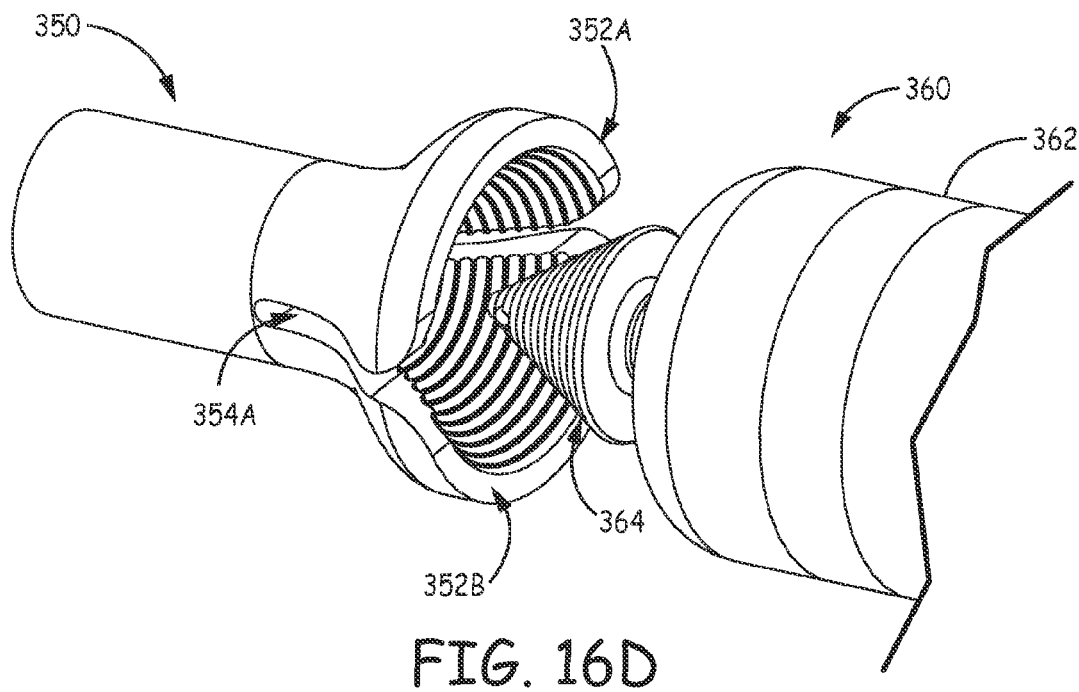
Figure 16E:
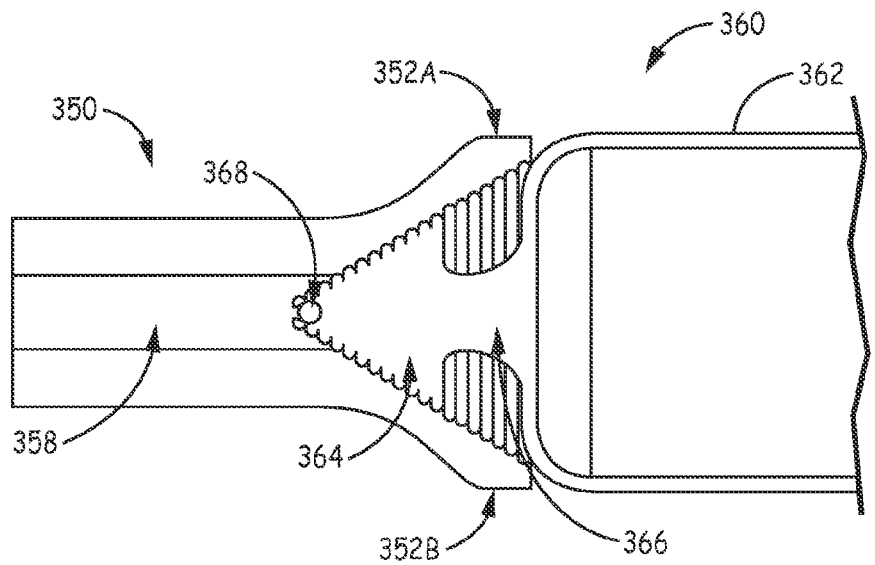

FIG. 16D is a perspective view and FIG. 16E is a cross-sectional view of the mating between cup structure 350 of FIGS. 16A-16C and proximal structure 364 of IMD 360. IMD 360 may be similar to IMD 26. IMD 360 also includes housing 362 to which proximal structure 364 is attached or formed with via neck 366. Proximal structure 364 also defines tether hole 368 through which a tether may be threaded. FIG. 16D shows proximal structure 364 within cup structure 350 but not yet contacting cup surface 356. FIG. 15E shows when proximal structure 364 is in contact with cup surface 356 of cup structure 350. A portion of proximal structure 364 may be disposed within lumen 358. As shown in FIG. 16E, each circumferential ridge of cup surface 356 on curved flanges 352 may mate with a respective circumferential ridge on proximal structure 364. In some examples, proximal structure 364 may "click" into cup structure 350 when the curved flanges 352 slightly bias outward and the circumferential ridges mate with each other. This frictional fit may be sufficient to transfer torque from elongated member 34 to IMD 360.

Figure 17A:
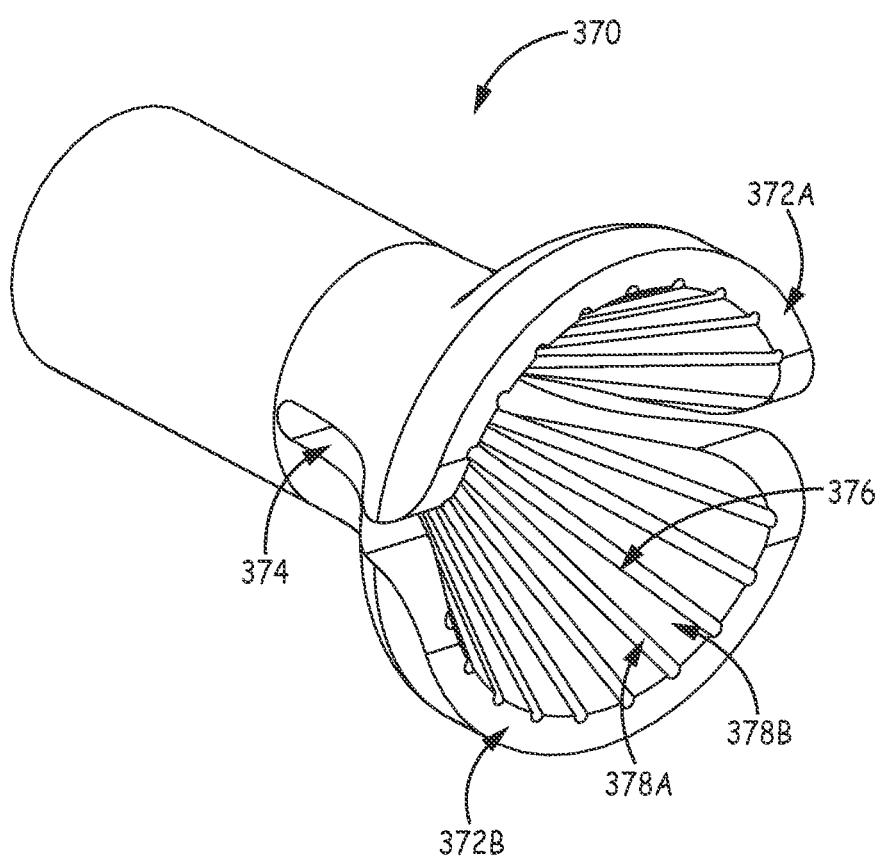
FIGS. 17A-17C are conceptual diagrams illustrating an example cup surface with longitudinal ridges at a distal end of an elongated member for friction fit mating with a structure of an IMD.
Figure 17B:
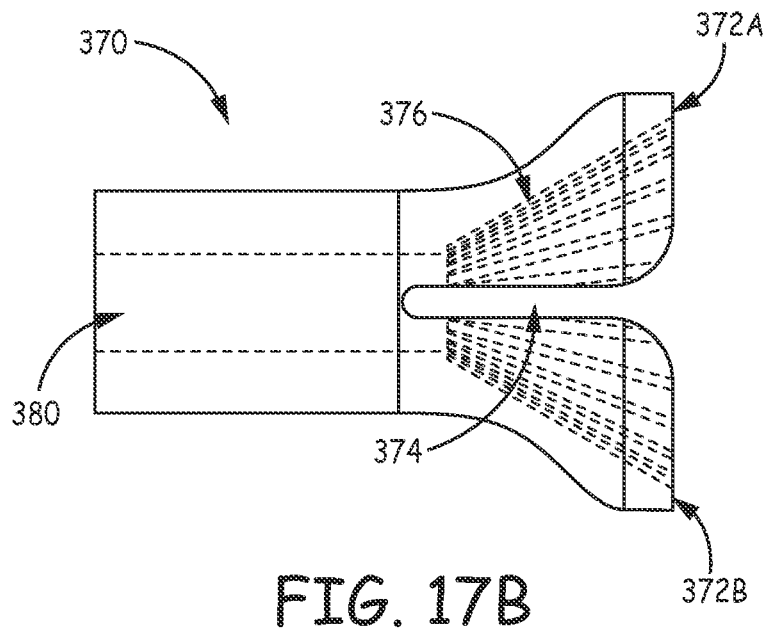
Figure 17C:
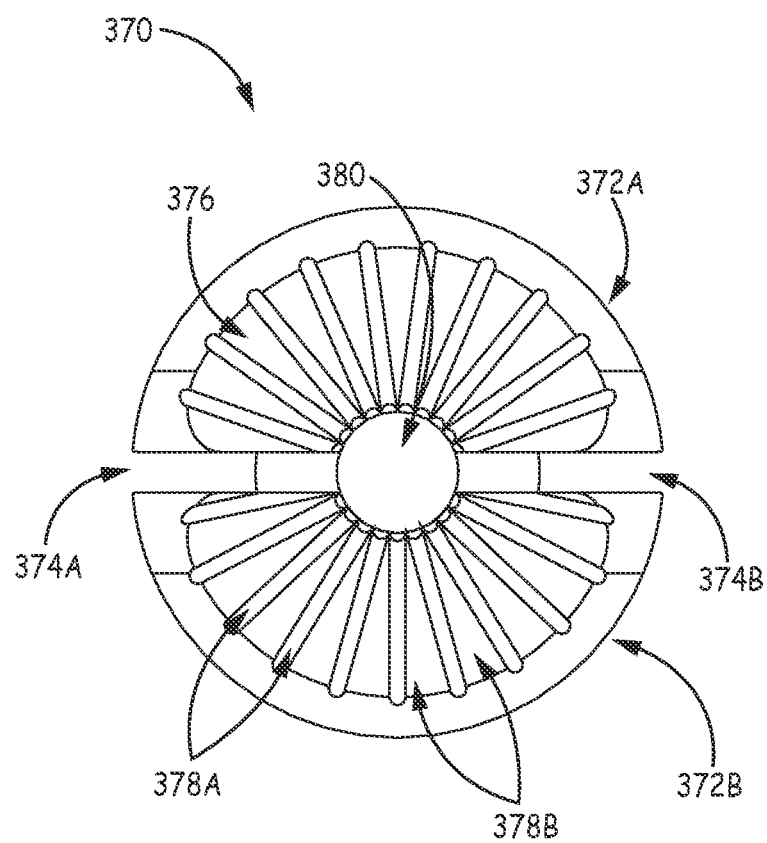

FIGS. 17A-17C are conceptual diagrams illustrating an example cup surface 376 with longitudinal ridges 378B at a distal end of an elongated member 34 for friction fit mating with a structure of an IMD. Cup structure 370 may be substantially similar to cup structure 350 of FIGS. 16A-16E. However, cup surface 376 includes longitudinal ridges 378B lining the inside of curved flanges 372A and 372B (collectively "curved flanges 372"). Longitudinal ridges 378B may be separated from each other by longitudinal channels 378A. The longitudinal channels 378A may be configured to mate with corresponding longitudinal ridges on the proximal structure of the IMD or longitudinal ridges 378B may mate with a smooth surface on the proximal structure of the IMD. Curved flanges 372 define slot 374 located between each of the curved flanges. Together, curved flanges 372 form cup surface 376 which may be conically shaped in some examples.

Side view FIG. 17B and top view FIG. 17C illustrates the various features of cup structure 370 such as curved flanges 372, cup surface 376, and lumen 378 formed by inner elongated member 34. Longitudinal ridges 378B and longitudinal channels 378A of cup surface 378 are also shown. In this manner, longitudinal ridges 378B and longitudinal channels 378A run outwards from lumen 380 toward the distal end of cup structure 370. Slots 374A and 374B are on opposing sides of lumen 378 and may allow for deflection and bias of curved flanges 372.

Various examples have been described. These and other examples are within the scope of the following claims. For example, although filtering of the physiological signal are directed to an electrical signal from the heart, this disclosure may also be applicable to other types of signals and blanking periods used for reasons other than a pacing pulse or defibrillation shock delivered to the patient. Furthermore, although described herein as implemented by an IMD and system including an IMD, in other examples, the techniques described herein may be implemented in an external medical device or signal processing device. An external medical device may be coupled to leads placed on the exterior surface of the patient, in some examples.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

Various examples have been described herein. Any combination of the described operations or functions is contemplated. These and other examples are within the scope of the following claims.

What is claimed is:

1. An implantable medical device delivery system, the system comprising:
   an elongated member comprising a first distal end and a first proximal end, the first distal end configured to mate with an implantable medical device having a fixation element;
   a resilient member defining a second distal end and a second proximal end, the resilient member disposed along at least a portion of the elongated member;
   a housing configured to accept the first proximal end of the elongated member and the second proximal end of the resilient member;
   a rotation control mechanism coupled to the housing and a portion of the elongated member, wherein user movement of the rotation control mechanism causes rotation of the elongated member with respect to the housing for rotating the fixation element of the implantable medical device into tissue; and
   a deflection control mechanism coupled to the housing and the second proximal end of the resilient member, wherein user movement of the deflection control mechanism causes longitudinal displacement of the resilient member along a longitudinal axis of the elongated member and the housing resulting in angular deflection of the first distal end of the elongated member, and wherein the deflection control mechanism allows rotation of the second proximal end of the resilient member about the longitudinal axis matching rotation of the elongated member caused by user movement of the rotation control mechanism.

2. The system of claim 1, wherein the elongated member is an inner elongated member, and wherein the system further comprises:
   an outer elongated member surrounding at least a portion of the inner elongated member, the outer elongated member configured to cover at least a portion of the implantable medical device; and
   a deployment mechanism coupled to the housing and a proximal end of the outer elongated member, the deployment mechanism comprising a slider coupled to the proximal end of the outer elongated member and defining an aperture through which the inner elongated member is allowed to rotate, wherein user movement of the deployment mechanism causes longitudinal displacement of the slider and the outer elongated member along the longitudinal axis with respect to the housing and the inner elongated member, and wherein proximal movement of the outer elongated member exposes the implantable medical device.

3. The system of claim 1, further comprising the implantable medical device, and wherein the implantable medical device comprises a helical fixation element.

4. The system of claim 1, wherein the elongated member comprises a keyed surface at the distal end of the elongated member, wherein the keyed surface is configured to mate with a keyed structure defined by the implantable medical device to translate rotational force from the elongated member to the implantable medical device.

5. The system of claim 1, wherein the housing defines a rib extending inwards towards a wheel of the rotation control mechanism, wherein the wheel comprises protrusions and depressions along an outer surface of the wheel, and wherein rotation of the rotation control mechanism and the wheel cause periodic contact episodes between the protrusions and the rib, each contact episode signaling an amount of rotational displacement of the elongated member.

6. The system of claim 1, wherein the rotation control mechanism comprises a rotation limiting structure, the rotation limiting structure coupled to the rotation control mechanism via mating threaded structures and configured to contact a portion of the housing after the rotation control mechanism rotates the elongated member a predetermined number of revolutions.

7. An implantable medical device delivery system, the system comprising:
   an elongated member comprising a first distal end and a first proximal end, the distal end configured to mate with an implantable medical device having a fixation element;
   a resilient member defining a second distal end and a second proximal end, the resilient member disposed along at least a portion of the elongated member;
   means for housing the first proximal end of the elongated member and the second proximal end of the resilient member;
   means for rotating the elongated member with respect to the means for housing the first proximal end of the elongated member for rotating the fixation element of the implantable medical device into tissue; and
   means for deflecting the first distal end of the elongated member via longitudinal displacement of the resilient member along a longitudinal axis of the elongated member, the deflection being angular deflection of the first distal end of the elongated member, and wherein the means for deflecting the first distal end of the elongated member allows rotation of the second proximal end of the resilient member about the longitudinal axis matching rotation of the elongated member caused by user movement of the means for rotating the elongated member.

8. The system of claim 7, wherein the elongated member is an inner elongated member, and wherein the system further comprises:
   an outer elongated member surrounding at least a portion of the inner elongated member, the outer elongated member configured to cover at least a portion of the implantable medical device; and
   a deployment mechanism coupled to the means for housing the first proximal end of the elongated member and a proximal end of the outer elongated member, the deployment mechanism comprising a slider coupled to the proximal end of the outer elongated member and defining an aperture through which the inner elongated member is allowed to rotate, wherein user movement of the deployment mechanism causes longitudinal displacement of the slider and the outer elongated member along the longitudinal axis with respect to the means for housing the first proximal end of the elongated member and the inner elongated member, and wherein proximal movement of the outer elongated member exposes the implantable medical device.

9. The system of claim 7, wherein:
the means for deflecting the first distal end of the elongated member comprises:
   a slider configured to move along the longitudinal axis, the slider comprising a protrusion extending out from the means for housing the first proximal end of the elongated member and a cylinder attached to the protrusion;
   a shaft comprising at least one rib extending longitudinally along an exterior surface of the shaft, wherein at least a portion of the shaft is disposed within the cylinder of the slider, and
   a collar defining an aperture, at least one channel extending radially outward from the aperture and longitudinally along the collar, and a mounting hole configured to mount the second proximal end of the resilient member, the at least one channel configured to mate with the at least one rib, wherein at least a portion of the collar is disposed between the cylinder and the shaft such that the collar can rotate within the cylinder and slide longitudinally along the shaft, and wherein user movement of the slider in the longitudinal direction causes longitudinal displacement of the collar and the resilient member; and
the means for rotating the elongated member comprises a wheel coupled to the means for housing the first proximal end of the elongated member and at least partially exposed externally from the means for housing the first proximal end of the elongated member, the wheel attached to and concentric with the portion of the elongated member, the wheel coupled to a distal end of the shaft of the means for deflecting the first distal end of the elongated member such that rotation of the wheel causes rotation of the shaft and the collar.

10. The system of claim 7, further comprising the implantable medical device, and wherein the implantable medical device comprises a helical fixation element.

11. The system of claim 7, wherein the elongated member comprises a keyed surface at the distal end of the elongated member, wherein the keyed surface is configured to mate with a keyed structure defined by the implantable medical device to translate rotational force from the elongated member to the implantable medical device.

12. The system of claim 7, wherein the means for housing the first proximal end of the elongated member defines a rib extending inwards towards a wheel of the means for rotating the elongated member, wherein the wheel comprises protrusions and depressions along an outer surface of the wheel, and wherein rotation of the means for rotating the elongated member and the wheel cause periodic contact episodes between the protrusions and the rib, each contact episode signaling an amount of rotational displacement of the elongated member.

13. The system of claim 7, wherein the means for rotating the elongated member comprises a rotation limiting structure, the rotation limiting structure coupled to the means for rotating the elongated member via mating threaded structures and configured to contact a portion of the means for housing the first proximal end of the elongated member after the means for rotating the elongated member rotates the elongated member a predetermined number of revolutions.

14. An implantable medical device delivery system, the system comprising:
   an elongated member comprising a first distal end and a first proximal end, the first distal end configured to mate with an implantable medical device having a fixation element;
   a resilient member defining a second distal end and a second proximal end, the resilient member disposed along at least a portion of the elongated member;
   a housing configured to accept the first proximal end of the elongated member and the second proximal end of the resilient member;
   a rotation control mechanism coupled to the housing and a portion of the elongated member, wherein user movement of the rotation control mechanism causes rotation of the elongated member with respect to the housing for rotating the fixation element of the implantable medical device into tissue; and
   a deflection control mechanism coupled to the housing and the second proximal end of the resilient member, wherein user movement of the deflection control mechanism causes longitudinal displacement of the resilient member along a longitudinal axis of the elongated member and the housing resulting in angular deflection of the first distal end of the elongated member, and wherein the deflection control mechanism comprises: a slider configured to move along the longitudinal axis, the slider comprising a protrusion extending out from the housing and a cylinder attached to the protrusion; a shaft comprising at least one rib extending longitudinally along an exterior surface of the shaft, wherein at least a portion of the shaft is disposed within the cylinder of the slider, and a collar defining an aperture, at least one channel extending radially outward from the aperture and longitudinally along the collar, and a mounting hole configured to mount the second proximal end of the resilient member, the at least one channel configured to mate with the at least one rib, wherein at least a portion of the collar is disposed between the cylinder and the shaft such that the collar can rotate within the cylinder and slide longitudinally along the shaft, and wherein user movement of the slider in the longitudinal direction causes longitudinal displacement of the collar and the resilient member; and the rotation control mechanism comprises a wheel coupled to the housing and at least partially exposed externally from the housing, the wheel attached to and concentric with the portion of the elongated member, the wheel coupled to a distal end of the shaft of the deflection control mechanism such that rotation of the wheel causes rotation of the shaft and the collar.

* * * * *